(12) United States Patent
Fu et al.

(10) Patent No.: US 7,795,457 B2
(45) Date of Patent: Sep. 14, 2010

(54) CARBAMATE COMPOUNDS

(75) Inventors: Hong Fu, Union City, CA (US);
Yaoquan Liu, Castro Valley, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 196 days.

(21) Appl. No.: 12/070,835

(22) Filed: Feb. 20, 2008

(65) Prior Publication Data
US 2008/0214617 A1  Sep. 4, 2008

Related U.S. Application Data

(60) Provisional application No. 60/903,770, filed on Feb. 26, 2007.

(51) Int. Cl.
*C07D 315/00* (2006.01)
(52) U.S. Cl. ..................................... 549/419
(58) Field of Classification Search .................. 549/419
See application file for complete search history.

(56) References Cited

U.S. PATENT DOCUMENTS

| | | | |
|---|---|---|---|
| 4,771,070 A | 9/1988 | Hokanson | |
| 4,792,522 A | 12/1988 | Nettleton | |
| 5,510,118 A | 4/1996 | Bosch | |
| 5,534,270 A | 7/1996 | De Castro | |
| 5,662,883 A | 9/1997 | Bagchi | |
| 6,420,591 B1 | 7/2002 | Rana et al. | |
| 2003/0162740 A1 | 8/2003 | Wang | |
| 2005/0203174 A1 | 9/2005 | Santi | |
| 2005/0272727 A1 | 12/2005 | Dong | |

FOREIGN PATENT DOCUMENTS

| | | |
|---|---|---|
| JP | 05-039283 A | 2/1993 |
| WO | WO 99/21870 | 5/1999 |
| WO | WO2007/033214 A2 | 3/2007 |

OTHER PUBLICATIONS

Nishi et al., J. Biol. Chem. (1994) 269(9): 6320-5324.
Fukuda et al., Nature (1997) 390: 308-311.
Kudo et al., Exp. Cell. Res. (1998) 242: 540-547.
Komiyama et al., J. Antibiotics (1985) 38(3): 427-429.
Hamamoto et al., J. Antibiotics (1983) 36(6): 639-645.
Newlands et al., Br. Cancer J. (1996) 74: 648-649.
Kalesse et al., Synthesis (2002) 8: 981-1003.
Kuhnt et al., Applied Environ. Microbiol. (1998) 64(2): 714-720.
Abe et al., J. Antibiotics (1993) 46(5): 735-740.
Abe et al., J. Antibiotics (1993) 46(5): 728-734.
Hosokawa et al., J. Antibiotics (1993) 46(4): 676-678.
Kobayashi et al., Tetrahedron Lett. (1998) 39(45): 8291-8294.
Kudo et al., Proc. Natl. Acad. Sci. USA (1999) 96(3): 9112-9117.
Meissner et al., FEBS Lett. (2004) 576: 27-30.
Vousden et al., Nat. Rev. Cancer (2002) 2: 594-604.
Lane et al., Proc. Natl. Acad. Sci. USA (2000) 97(15): 8501-8506.
Peehl et al., Prostate (2003) 54: 258-267.
Vigneri et al., Nature Medicine (2001) 7: 228-234.

*Primary Examiner*—D. Margaret Seaman
*Assistant Examiner*—Nizal S Chandrakumar
(74) *Attorney, Agent, or Firm*—Laurelee A. Duncan

(57) ABSTRACT

Carbamate compounds having a structure represented by formula I (where $R^1$, $R^2$, $R^3$, $R^4$, $R^5$ and $R^6$ are as defined herein) are useful as anti-tumor agents.

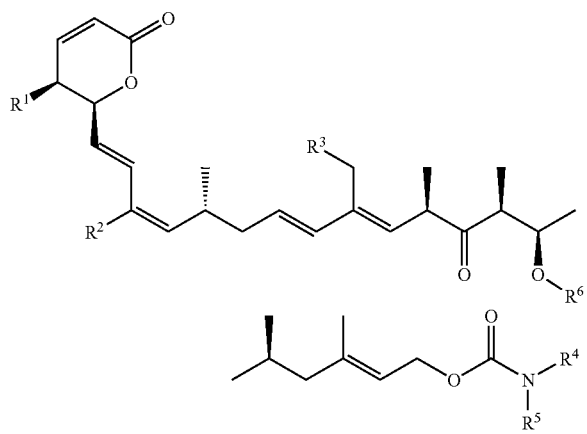

9 Claims, 15 Drawing Sheets

Figure 4:
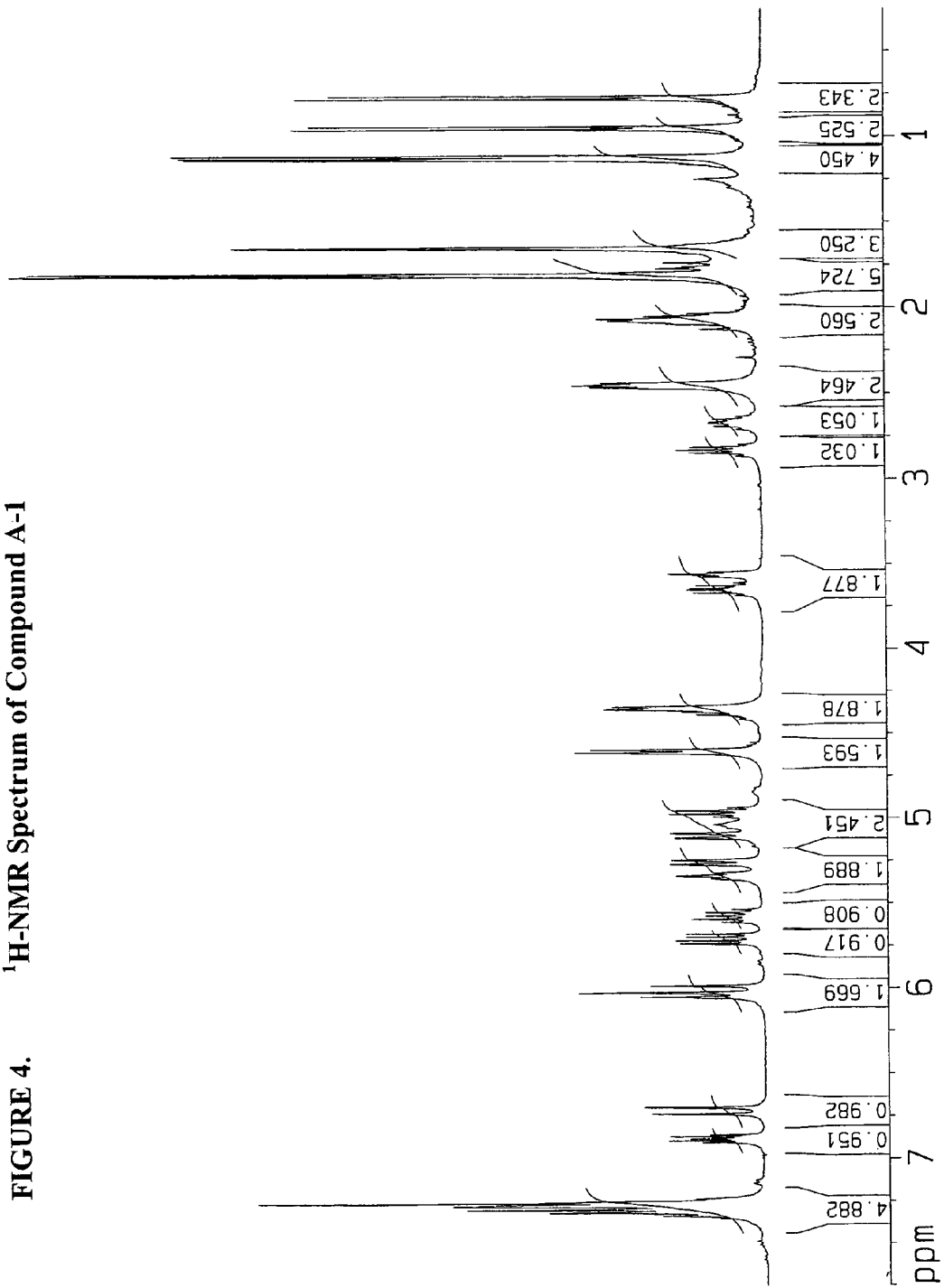

FIGURE 4. ¹H-NMR Spectrum of Compound A-1

Figure 5:
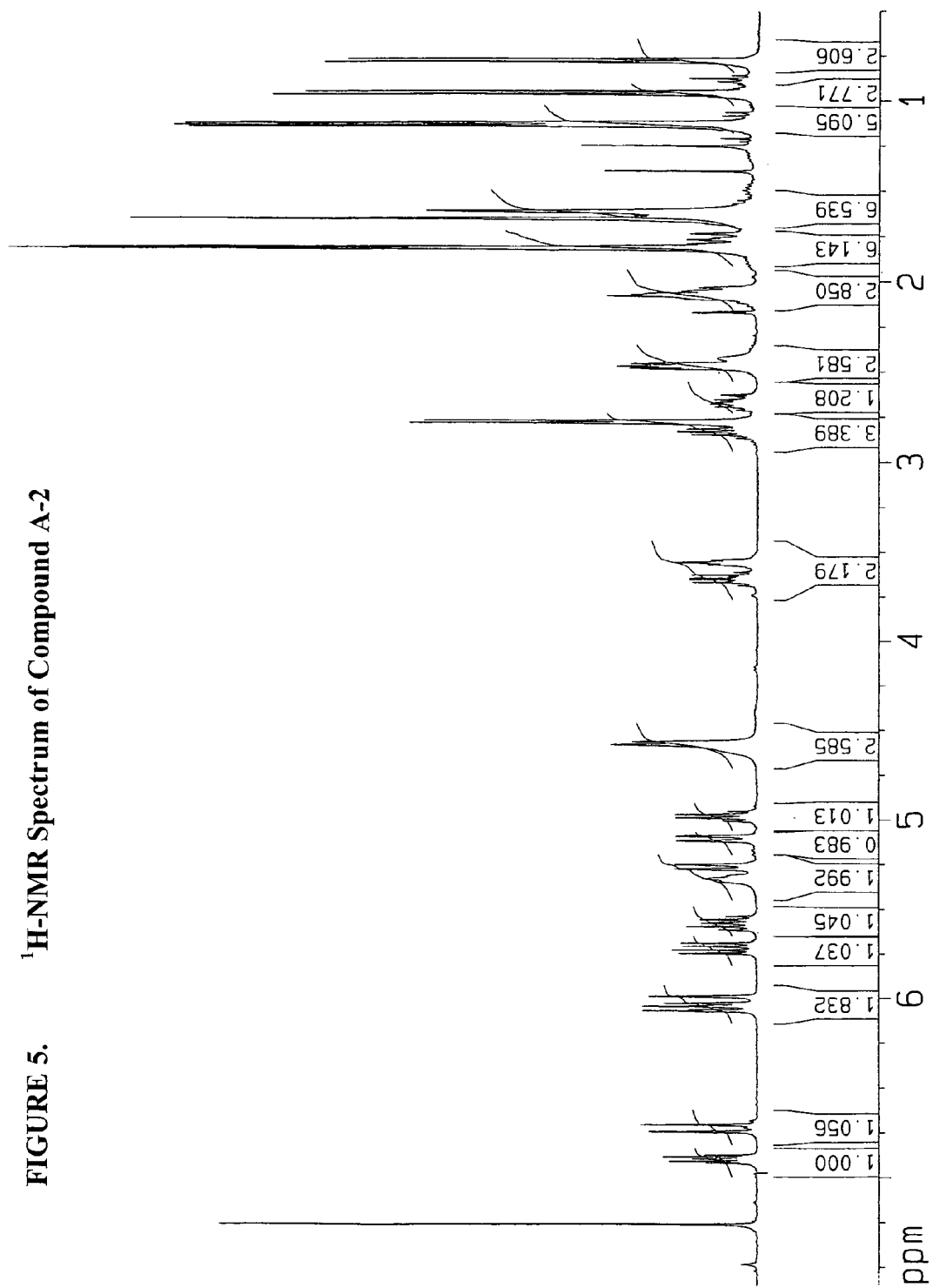

FIGURE 5.  $^1$H-NMR Spectrum of Compound A-2

Figure 6:
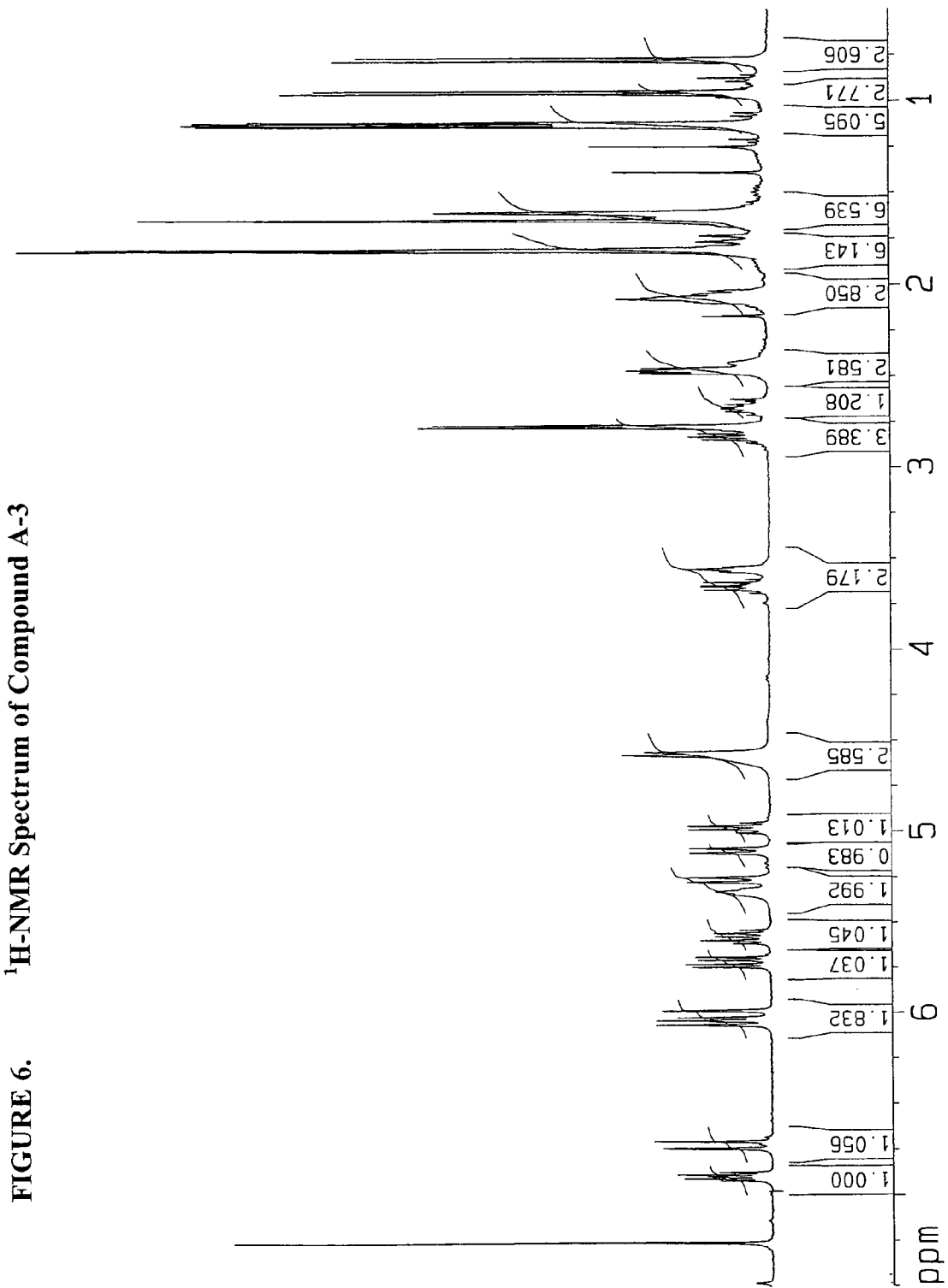

FIGURE 6. ¹H-NMR Spectrum of Compound A-3

Figure 7:
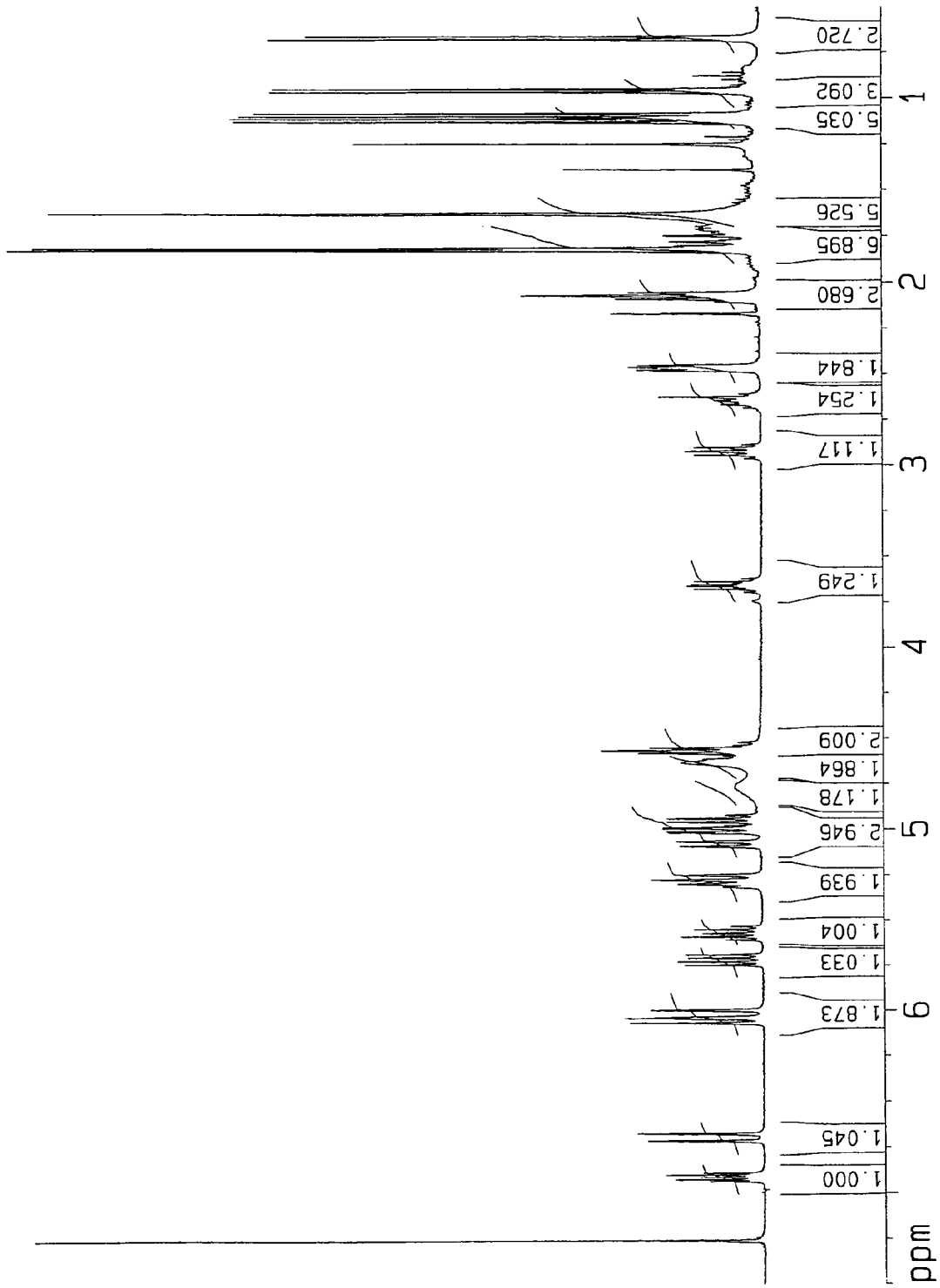

FIGURE 7. ¹H-NMR Spectrum of Compound A-4

Figure 8:
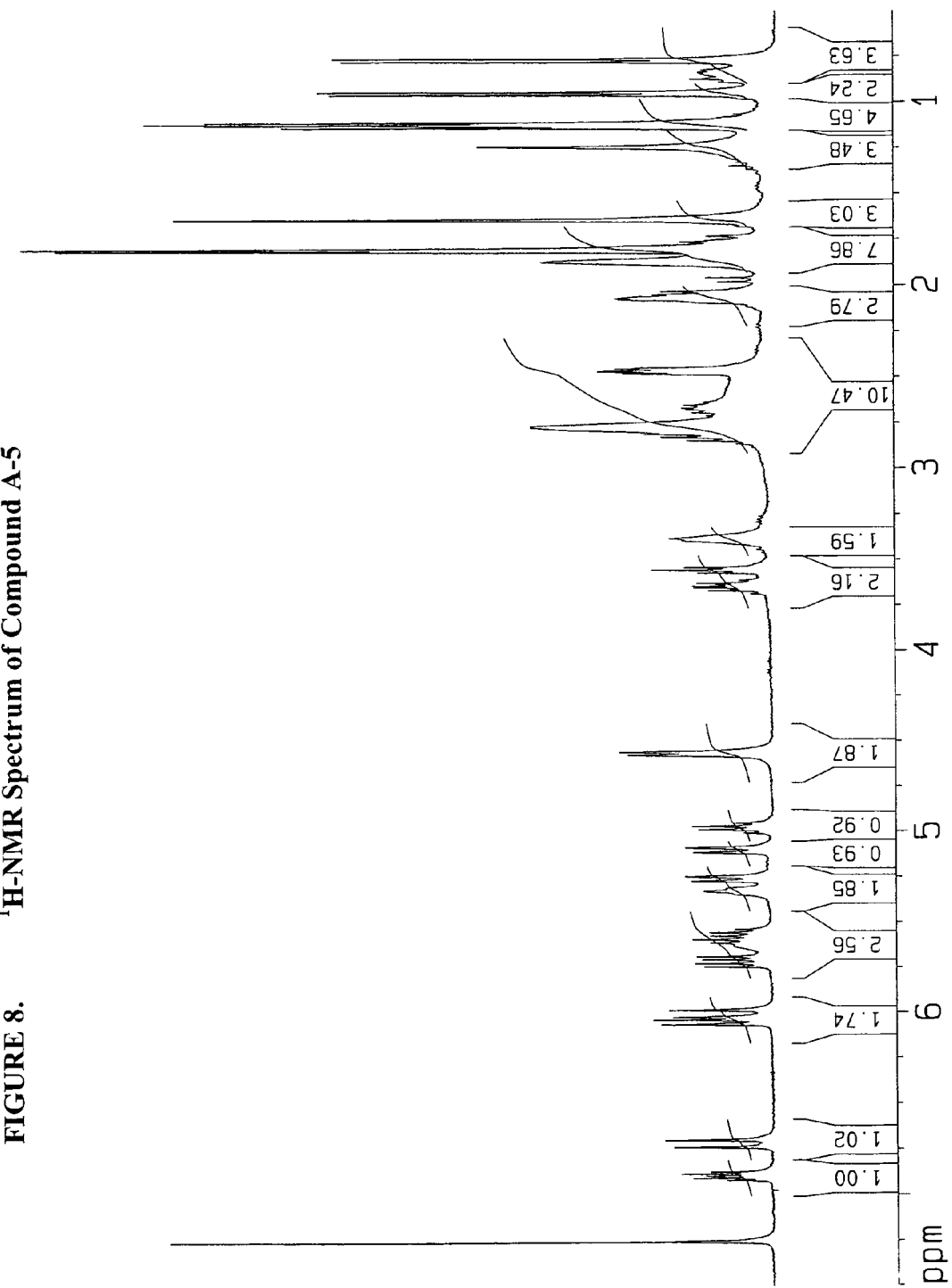

FIGURE 8. ¹H-NMR Spectrum of Compound A-5

Figure 9:
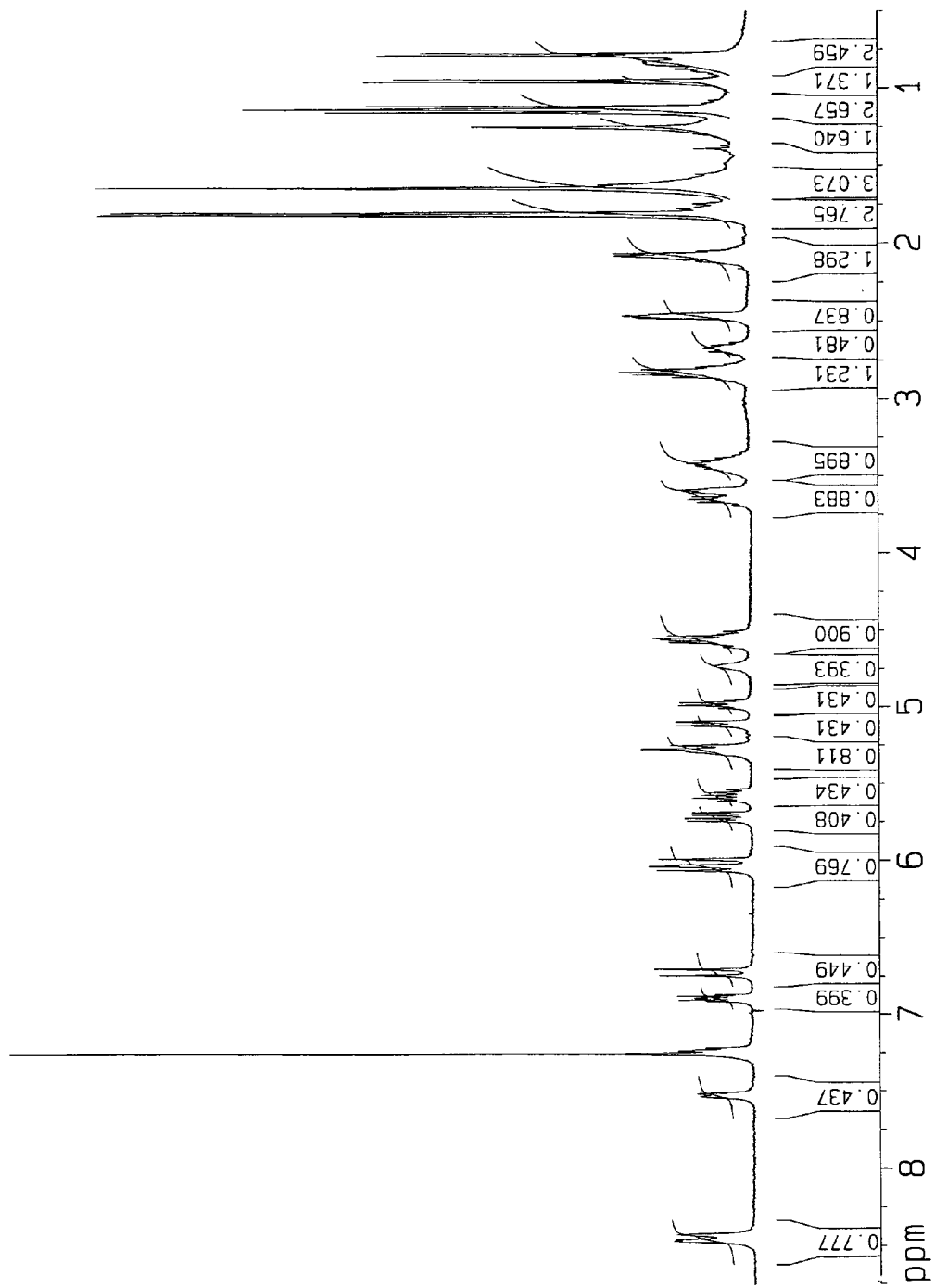

FIGURE 9. ¹H-NMR Spectrum of Compound A-6

Figure 10:
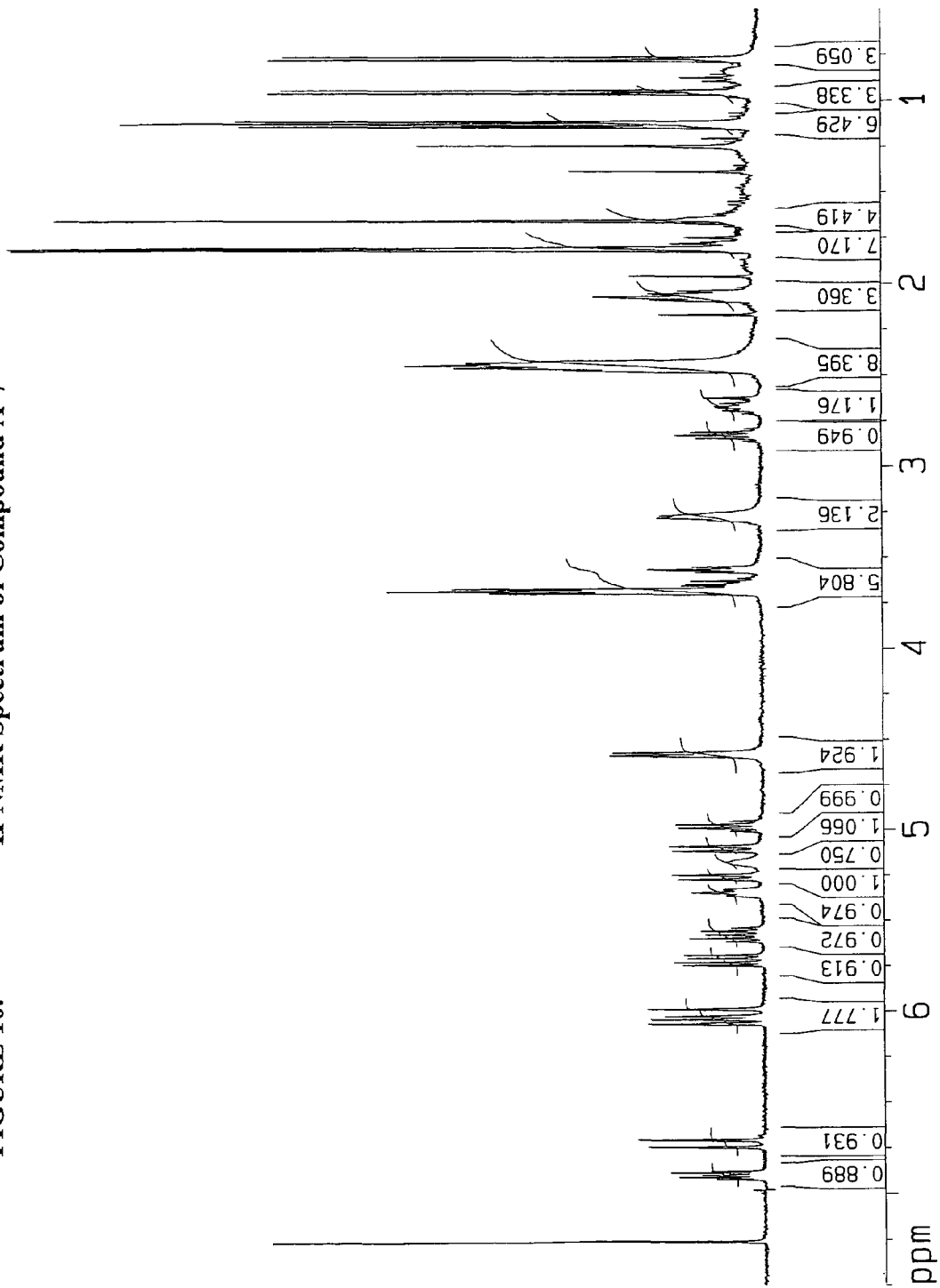

FIGURE 10. $^1$H-NMR Spectrum of Compound A-7

Figure 11:
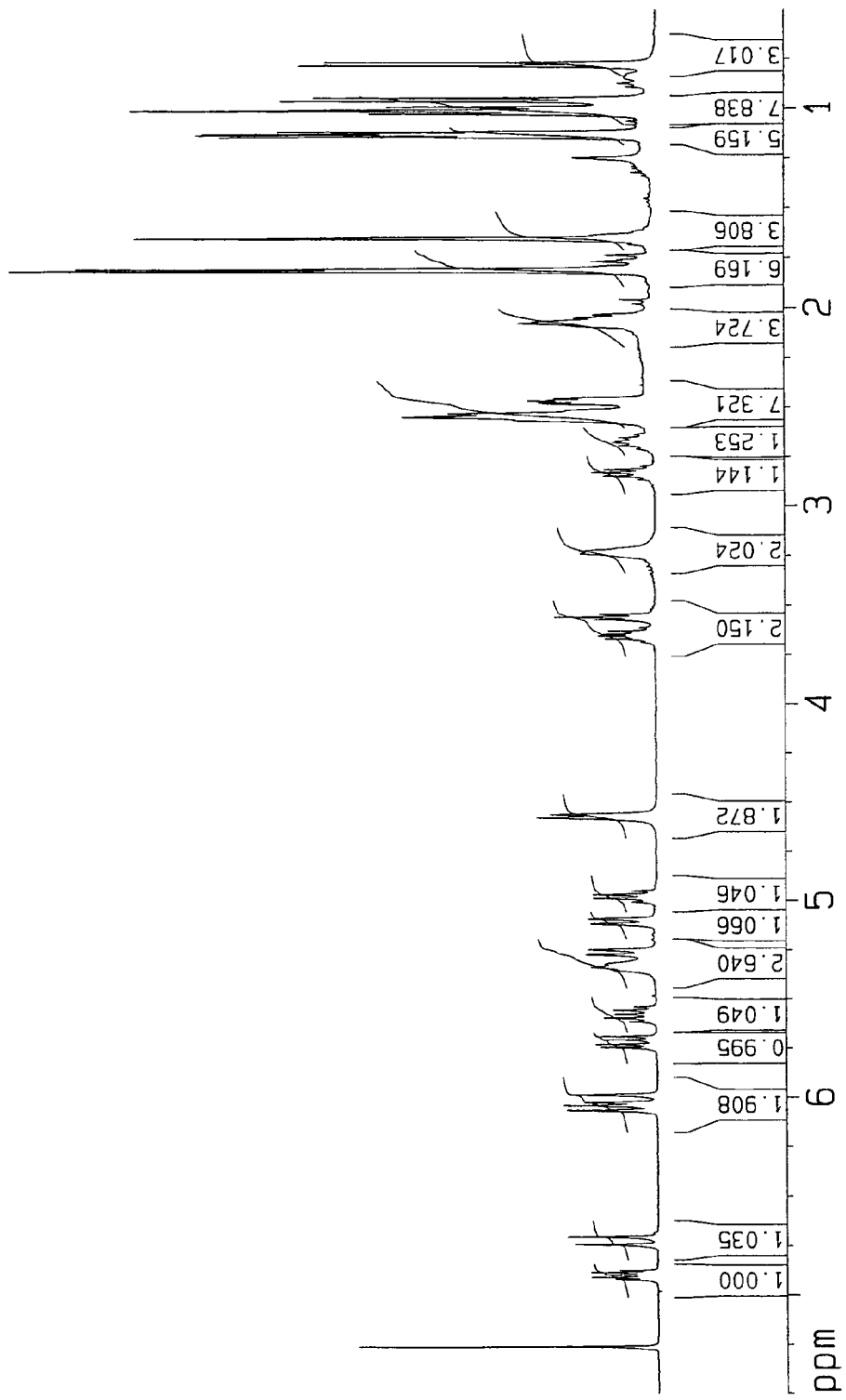

FIGURE 11. ¹H-NMR Spectrum of Compound A-8

$^1$H-NMR Spectrum of Compound A-9

Figure 13:
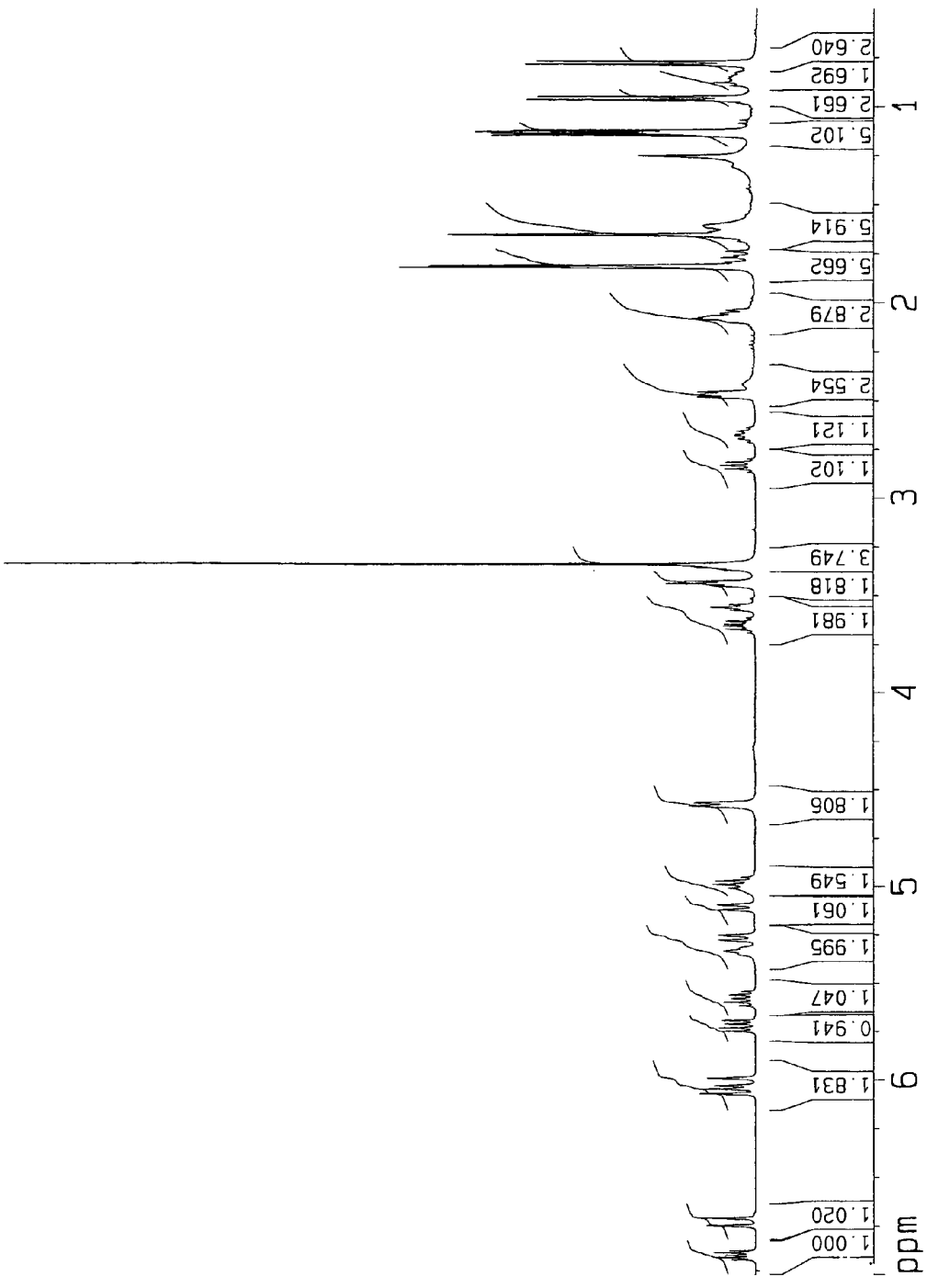

FIGURE 13. $^1$H-NMR Spectrum of Compound A-10

$^1$H-NMR Spectrum of Compound A-11

$^1$H-NMR Spectrum of Compound A-12

CARBAMATE COMPOUNDS

CROSS-REFERENCE TO RELATED APPLICATIONS

This application claims the benefit under 35 U.S.C. §119(e) of U.S. Provisional Application No. 60/903,770 filed Feb. 26, 2007, the disclosure of which is incorporated herein by reference.

STATEMENT REGARDING FEDERALLY SPONSORED RESEARCH OR DEVELOPMENT

This invention was made in part with Government support under Grant No. 5 R43 CA109840-02 awarded by the National Institutes of Health. The Government has certain rights in this invention.

BACKGROUND OF THE INVENTION

1. Field of the Invention

This invention relates to carbamate compounds having utility as anti-cancer agents and methods for their preparation and use.

2. Description of Related Art

The passage of proteins into and out of the nucleus of eukaryotic cells is a tightly controlled active transport process, referred to as nuclear import (or export). A protein to be transported contains a characteristic short amino acid sequence, called a nuclear localization sequence ("NLS") or a nuclear export sequence ("NES") identifying it as "cargo protein" to be imported or exported, respectively. A transport factor protein recognizes the NLS or NES and binds to the cargo protein and ferries it across the nuclear pore complex, which is the portal through which entry into and exit from the nucleus occurs. A transport factor that mediates nuclear import is called an importin; conversely, one that mediates nuclear export is called an exportin.

An exportin is CRM1, also referred to as exportin 1. Another protein involved in nuclear export is Ran, which is found in a guanine triphosphate bound form ("Ran-GTP") and a guanine diphosphate bound form ("Ran-GDP"). Inside the nucleus, CRM1 forms a ternary complex with Ran-GTP and a cargo protein. The complex exits the nucleus through the nuclear pore complex and into the cytoplasm. There, the protein RanGAP activates the intrinsic ATPase activity of Ran-GTP, converting it to Ran-GDP and causing the ternary complex to dissociate and release the cargo protein. Then CRM1 re-enters the nucleus, to start the cycle anew. If nuclear export is inhibited, normal cell cycle progression is disrupted and apoptosis may occur.

Leptomycin B ("LMB", formerly known as elactocin, NSC 364372, or PD 114720) is an anti-tumor, anti-microbial natural product originally isolated from *Streptomyces* spp., as reported in Hokanson et al., U.S. Pat. No. 4,771,070 (1988) and Nettleton et al., U.S. Pat. No. 4,792,522 (1988).

Subsequently, it was discovered that LMB is a covalent inhibitor of CRM1. Among the CRM1 cargo proteins whose nuclear export is consequently inhibited by LMB are p53, p73, STAT1, (i)ADAR1, Rev, actin, and Bcr-ab1. See, e.g., Nishi et al., *J. Biol. Chem.* 1994, 269 (9), 6320-6324; Fukuda et al., *Nature* 1997, 390, 308-311; Kudo et al., *Exp. Cell Res.* 1998, 242, 540-547. Many of these cargo proteins are implicated in cancer, leading to interest in LMB as a potential anti-cancer agent. Komiyama et al., *J. Antibiotics* 1985, 38 (3), 427-429; Wang et al., US 2003/0162740 A1 (2003). However, the cytotoxicity of LMB towards mammalian cells (Hamamoto et al., *J. Antibiotics* 1983, 36 (6), 639-645) offsets its potential as an anti-cancer agent. A phase 1 trial of LMB was halted in 1994 due to extreme toxicity. Newlands et al., *Br. Cancer J.* 1996, 74, 648-649.

LMB is the archetype of a natural product family referred to as the leptomycin family, characterized by a 2,3-dehydro-δ-valerolactone ring at one end of the molecule ($C_1$-$C_5$) and an extended carbon chain having a 6E,8Z and a 12E,14E diene system located off $C_5$. For a review on the chemistry and biology of the leptomycin family, see Kalesse et al., *Synthesis* 2002, 8, 981-1003. Other members of the leptomycin family include leptomycin A, ratjadone, anguinomycins A-D, callystatin A, kazusamycin A (formerly known as CL-1957A), kazusamycin B (formerly known as CL-1957E), leptolstatin, and leptofuranins A-D. The structures of some of the other members of the leptomycin family are shown below:

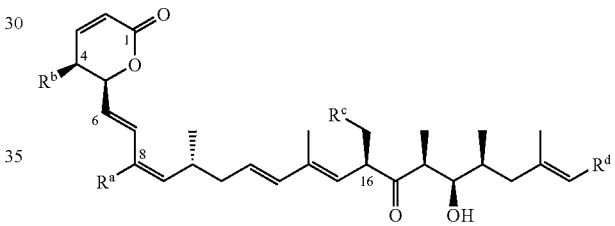

| | | | | |
|---|---|---|---|---|
| Leptolstatin: | $R^a$ = Me | $R^b$ = H | $R^c$ = H | $R^d$ = CH$_2$OH |
| Leptomycin A: | $R^a$ = Me | $R^b$ = Me | $R^c$ = H | $R^d$ = CO$_2$H |
| Anguinomycin A: | $R^a$ = Me | $R^b$ = H | $R^c$ = H | $R^d$ = CO$_2$H |
| Anguinomycin B: | $R^a$ = Et | $R^b$ = H | $R^c$ = H | $R^d$ = CO$_2$H |
| Kazusamycin A: | $R^a$ = Et | $R^b$ = Me | $R^c$ = OH | $R^d$ = CO$_2$H |
| Kazusamycin B: | $R^a$ = Me | $R^b$ = Me | $R^c$ = OH | $R^d$ = CO$_2$H |

Studies on the structure activity relationship of the leptomycin family compounds have been sparse. Kudo et al., supra, showed that the nitromethyl valerolactone derivative of LMB is inactive, suggesting that the 2,3-dehydro-δ-valerolactone moiety is an essential pharmacophore. Kuhnt et al., *Applied Environ. Microbiol.* 1998, 64 (2), 714-720, subjected LMB to bioconversion by a number of bacteria and fungi, resulting in several derivatives. Dong et al., US 2005/0272727 A1 (2005) and Dong et al., WO 2007/033214

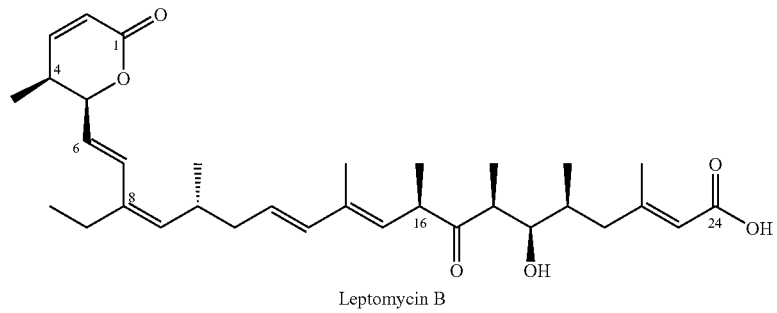

Leptomycin B (2007), disclose amides and esters, respectively, of leptomycin family compounds.

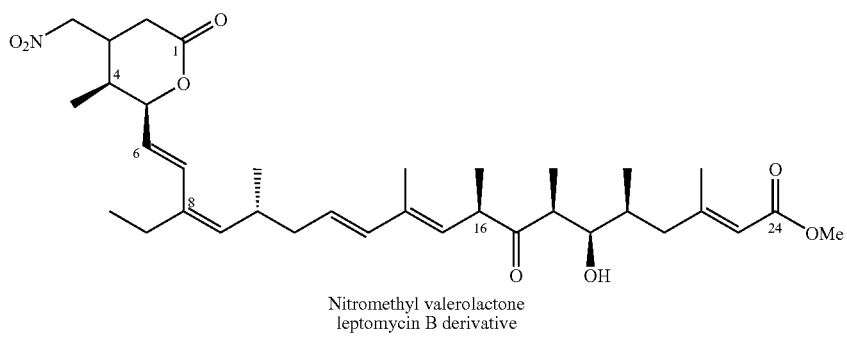

Nitromethyl valerolactone
leptomycin B derivative

The disclosures of the documents cited in this section are incorporated herein by reference.

BRIEF SUMMARY OF THE INVENTION

The present invention provides compounds that are useful as anti-cancer agents and are structurally related to the leptomycin family.

In a first embodiment, there is provided a compound having a structure represented by formula I

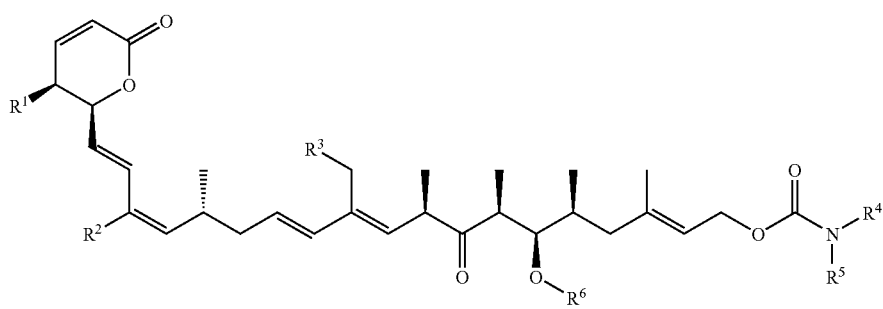

(I)

or a pharmaceutically acceptable salt thereof,
where
$R^1$ is H or $C_1$-$C_5$ alkyl;
$R^2$ is $C_1$-$C_5$ alkyl;
$R^3$ is H or OH;
$R^4$ and $R^5$ are independently, for each occurrence thereof, H, $C_1$-$C_8$ alkyl, $C_2$-$C_8$ alkenyl, $C_2$-$C_8$ alkynyl, $CHR^7R^9$, or $(CHR^9)_nR^8$, or $R^4$ and $R^5$ together with the nitrogen to which they are bonded combine to form

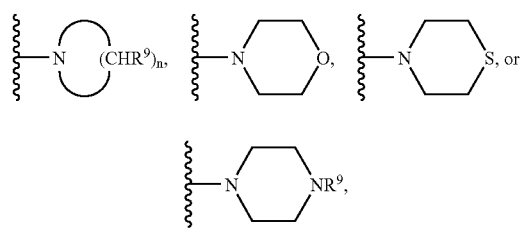

with the proviso that $R^5$ can also be $C(=O)NH_2$;
$R^6$ is H or $C(=O)NR^4R^5$;

$R^7$ is unsubstituted or substituted aryl, unsubstituted or substituted heteroaryl, unsubstituted or substituted cycloaliphatic, unsubstituted or substituted heterocycloaliphatic, $CO_2R^9$, cyano, or $COR^9$;

$R^8$ is unsubstituted or substituted aryl, unsubstituted or substituted heteroaryl, unsubstituted or substituted cycloaliphatic, unsubstituted or substituted heterocycloaliphatic, $NR^4R^5$, $CO_2R^9$, OH, halo, cyano, $OR^9$, or $COR^9$;

$R^9$ is, independently for each occurrence thereof, H, OH or $C_1$-$C_5$ alkyl; and n is, independently for each occurrence thereof, 2, 3, 4, 5, or 6.

In a second embodiment, there is provided a method for inhibiting the proliferation of a target cell, comprising contacting the target cell with an effective amount of a compound of this invention. The target cell can be a cancer cell, especially a bladder cancer, breast cancer, cervical cancer, CNS cancer, colon cancer, head and neck cancer, leukemia, liver cancer, lung cancer, melanoma, ovarian cancer, pancreatic cancer, prostate cancer, or renal cancer cell.

In a third embodiment, there is provided a method for treating a hyperproliferative disease, comprising administering to a patient suffering from such hyperproliferative disease a therapeutically effective amount of a compound of this invention. The hyperproliferative disease so treated can be cancer, especially bladder cancer, breast cancer, cervical cancer, CNS cancer, colon cancer, head and neck cancer, leukemia, liver cancer, lung cancer, melanoma, ovarian cancer, pancreatic cancer, prostate cancer, or renal cancer. The patient preferably is a mammal, especially a human.

In a fourth embodiment, there is provided the use of a compound of this invention for the preparation of a medicament for treating a hyperproliferative disease, which can be cancer, especially bladder cancer, breast cancer, cervical cancer, CNS cancer, colon cancer, head and neck cancer, leukemia, liver cancer, lung cancer, melanoma, ovarian cancer, pancreatic cancer, prostate cancer, or renal cancer.

In a fifth embodiment, there is provided a pharmaceutical formulation comprising a compound of this invention and an excipient.

In a sixth embodiment, there is provided a method of inhibiting the export of a protein from the nucleus of a cell via a CRM1-mediated process, comprising contacting said cell with an inhibitory amount of a compound according to this invention.

BRIEF DESCRIPTION OF THE DRAWING(S)

Figure 1:
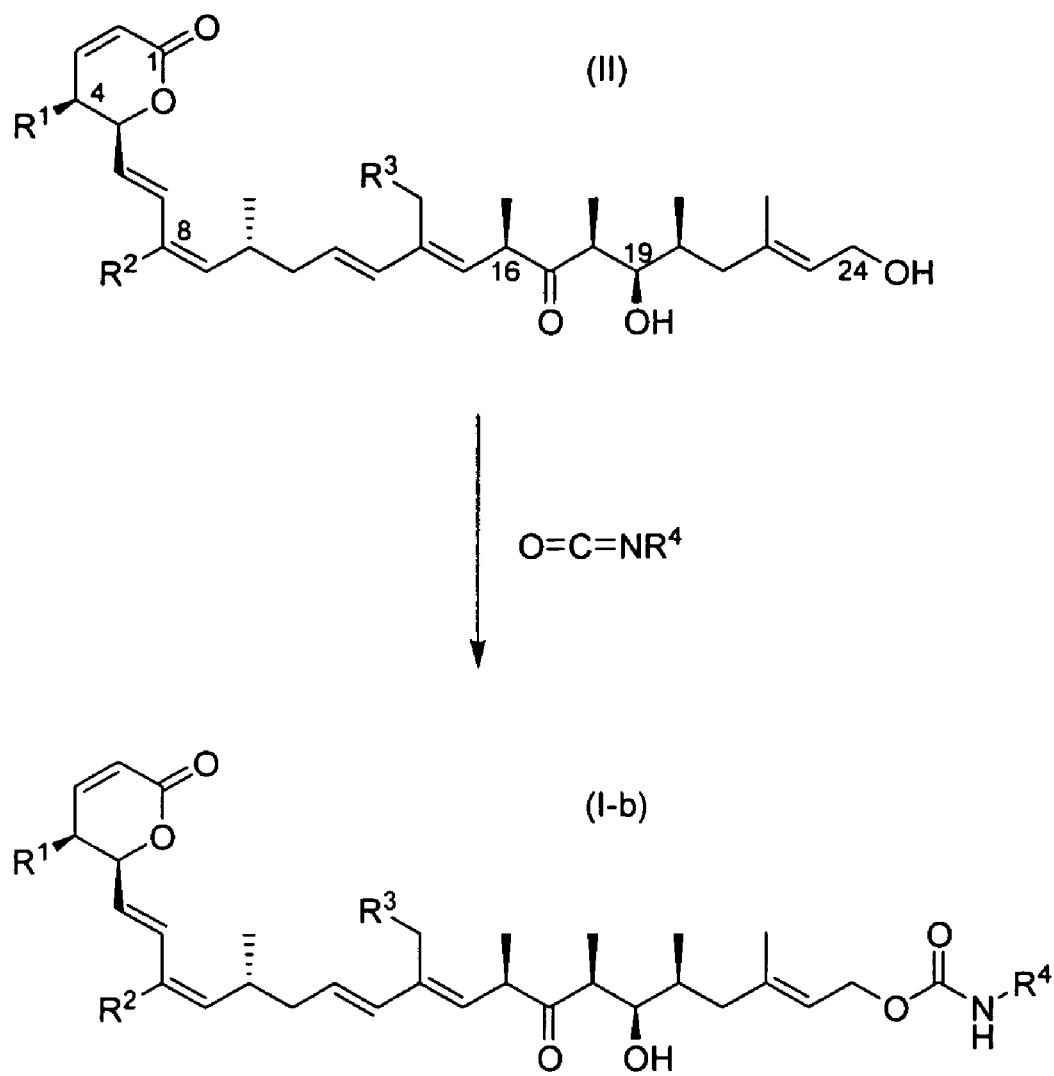
Figure 2:
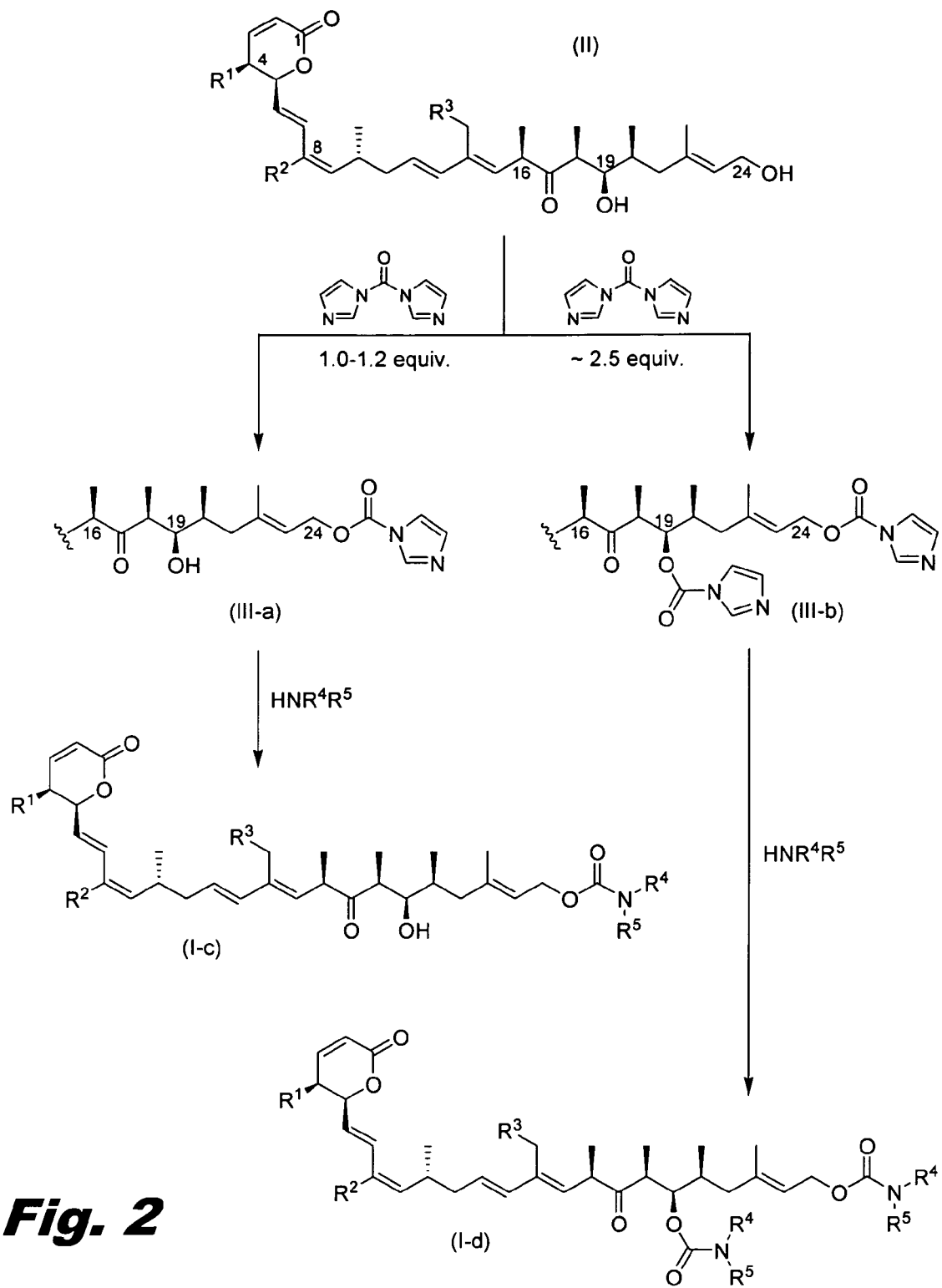
Figure 3:
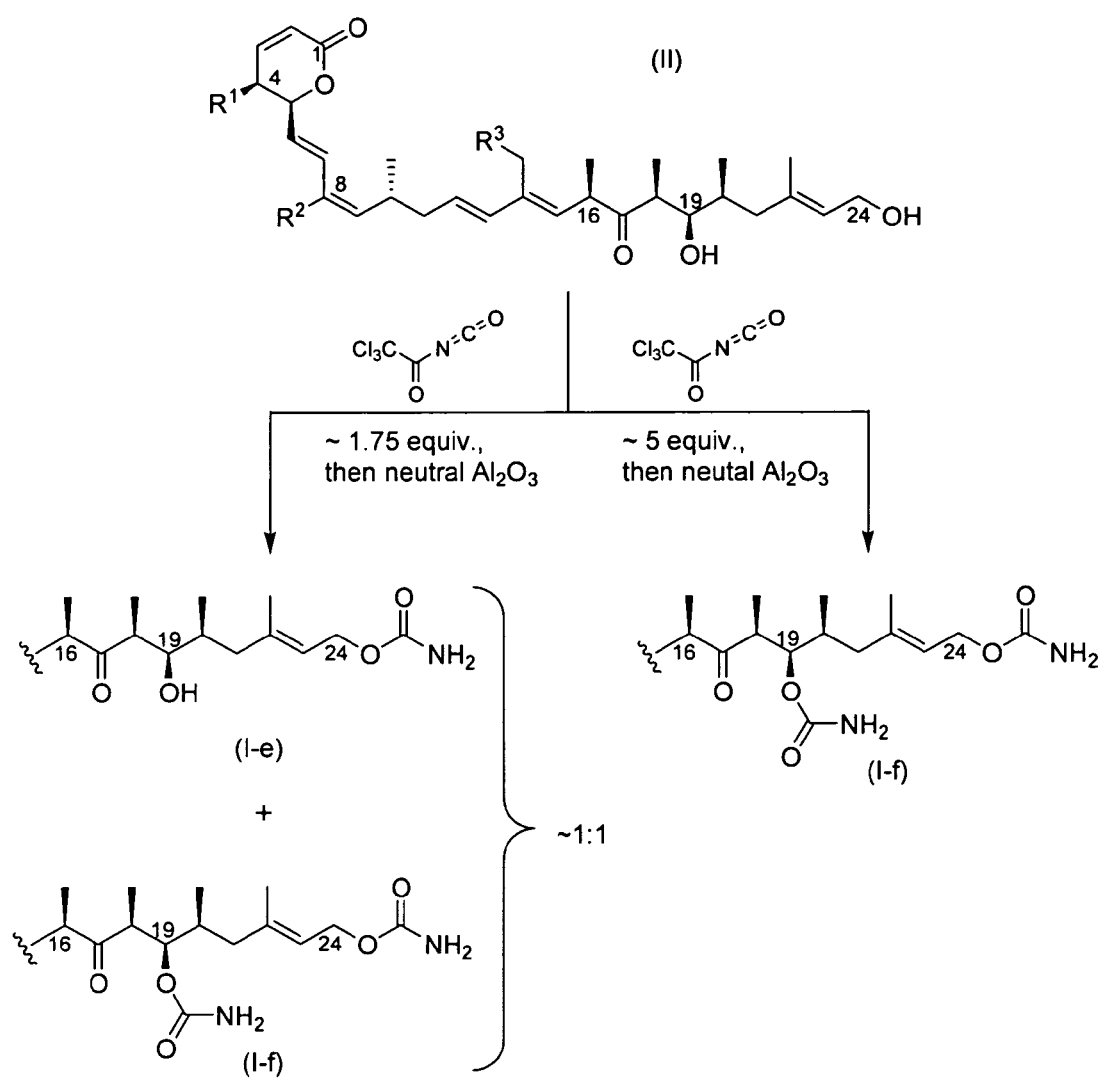

FIGS. 1, 2, and 3 depict first, second, and third schemes for the synthesis of compounds of this invention.

FIGS. 4 through 15 show $^1$H-NMR spectra for compounds of this invention.

DETAILED DESCRIPTION OF THE INVENTION

Definitions

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_5$ alkyl moieties include, but are not limited to, methyl, ethyl, propyl, isopropyl, isobutyl, t-butyl, 1-butyl, 2-butyl, n-pentyl, and the like.

"Alkenyl" means an aliphatic moiety having at least one carbon-carbon double bond, with the same convention for designating the number of carbon atoms being applicable. By way of illustration, $C_2$-$C_5$ alkenyl moieties include, but are not limited to, ethenyl (vinyl), 2-propenyl (allyl or prop-2-enyl), cis-1-propenyl, trans-1-propenyl, E- (or Z-)2-butenyl, 3-butenyl, 1,3-butadienyl (but-1,3-dienyl), 1-pentenyl, and the like.

"Alkynyl" means an aliphatic moiety having at least one carbon-carbon triple bond, with the same convention for designating the number of carbon atoms being applicable. By way of illustration, $C_2$-$C_5$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings and each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydro-thiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Alkoxy", "aryloxy", "alkylthio", and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolinyl, quinazolinyl, cinnolinyl, quinozalinyl, naphthyridinyl, benzo-furanyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like.

Where it is indicated that a moiety may be substituted, such as by use of "substituted or unsubstituted" or "optionally substituted" phrasing as in "substituted or unsubstituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl", (heterocycloaliphatic)alkyl", "arylalkenyl", "arylalkynyl", "biarylalkyl", and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl", "alkenylcycloalkyl", and the like mean an aryl, cycloalkyl, etc., moiety, as the case may be, substituted with an alkyl, alkenyl, etc., moiety, as the case may be, for example as in methylphenyl(tolyl) or allylcyclohexyl. "Hydroxyalkyl", "haloalkyl", "alkylaryl", "cyanoaryl", and the like mean an alkyl, aryl, etc., moiety, as the case may be, substituted with one or more of the identified substituent (hydroxyl, halo, etc., as the case may be).

By way of illustration, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(atkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(cycloalkyl), —O(heterocycloalkyl), —O(aryl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxy-alkyl), —C(=O)(alkyl), —C(=O)H, —CO$_2$H, —C(=O)NHOH, —C(=O)O(alkyl), —C(=O)O(hydroxy-alkyl), —C(=O)NH$_2$, —C(=O)NH(alkyl), —C(=O)N(alkyl)$_2$, —OC(=O)(alkyl), —OC(=O)(hydroxy-alkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Preferred substituents for aryl, heteroaryl, heteroaliphatic, and heterocycloaliphatic groups of this invention include $C_1$-$C_5$ alkyl, $C_2$-$C_5$ alkenyl, $C_2$-$C_5$ alkynyl, halo (especially fluoro or chloro), O($C_1$-$C_5$ alkyl), OCF$_3$, CF$_3$, CF$_2$CF$_3$, cyano, nitro, C(=O)($C_1$-$C_5$ alkyl), OH, O(CH$_2$)$_m$OH, O(CH$_2$)$_m$O($C_1$-$C_5$ alkyl), and O(CH$_2$)$_m$(halo), where m is 2, 3, or 4.

Where a range is stated, as in "$C_1$ to $C_5$ alkyl" or "5 to 10%," such range includes the end points of the range.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, citrate, maleate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclo-hexylamine salt, benzathine salt, sodium salt, tetramethylammonium salt, and the like. Polymorphic crystalline forms and solvates are also encompassed within the scope of this invention.

Compounds and Methods

In a preferred embodiment, $R^1$ is H or Me in formula I. In another preferred embodiment, $R^2$ is Me or Et in formula I. In another preferred embodiment, $R^1$ is H or Me and $R^2$ is Me or Et in formula I.

In another preferred embodiment, each of $R^4$ and $R^5$ are devoid of functional groups that are ionized at physiological pH.

In another preferred embodiment, $R^1$ is H, $R^2$ is Me, and $R^3$ is H in formula I, corresponding to a compound having a structure represented by formula I-a:

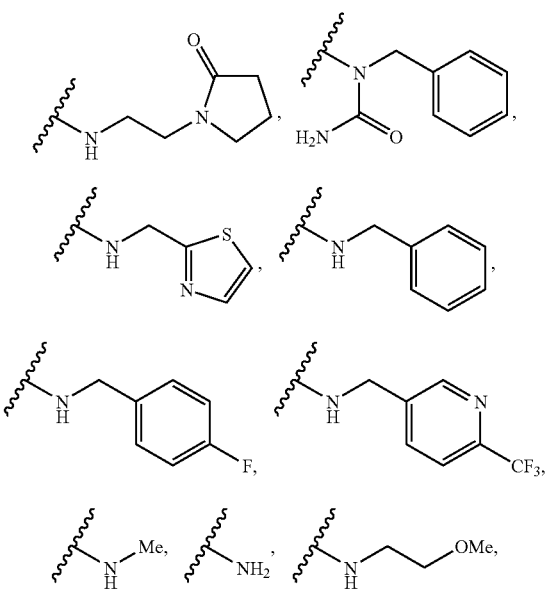

(I-a)

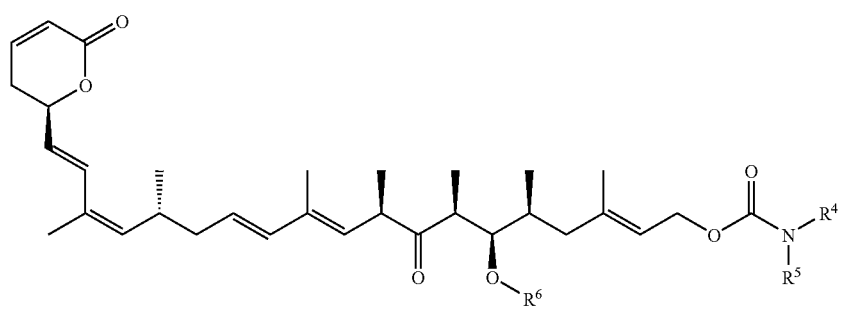

In a preferred embodiment of compounds of formula I or I-a, $R^5$ is H. In another preferred embodiment of compounds according to formula I or I-a, $R^6$ is H. In yet another preferred embodiment of compounds according to formula I or I-a, each of $R^5$ and $R^6$ is H.

In another preferred embodiment, in formula I $R^4$ and $R^5$ are independently, for each occurrence thereof, H, $C_1$-$C_8$ alkyl, $C_2$-$C_8$ alkenyl, $C_2$-$C_8$ alkynyl, $CHR^7R^9$, or $(CHR^9)_nR^8$, or $R^4$ and $R^5$ together with the nitrogen to which they are bonded combine to form

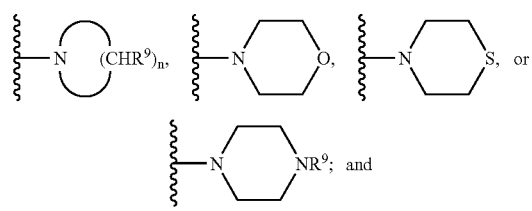

$R^9$ is, independently for each occurrence thereof, H or $C_1$-$C_5$ alkyl.

Preferred groups $NR^4R^5$ in formula I or I-a include:

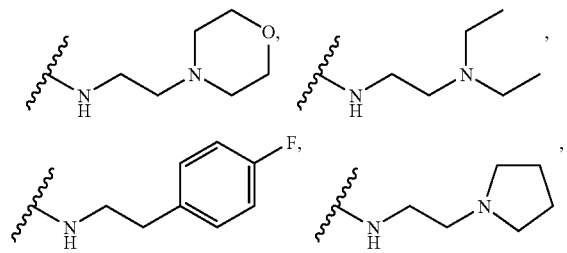

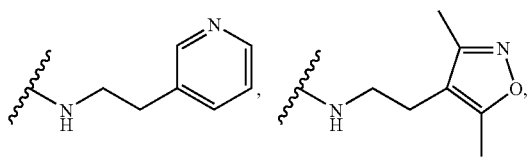

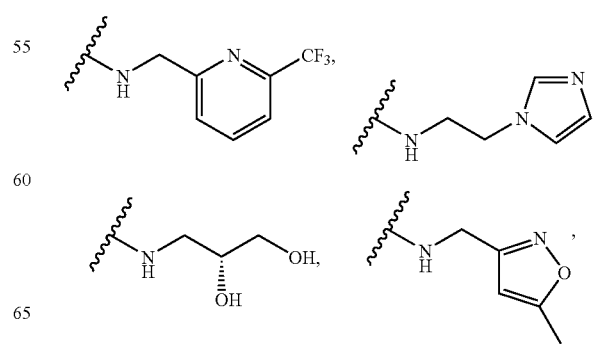

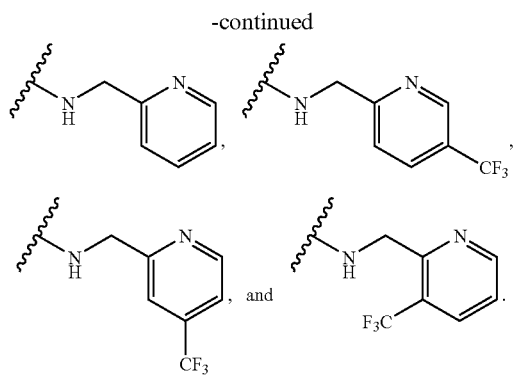

Examples of compounds of this invention are listed in Table A.

Table A

| Compound | R¹ | R² | R³ | NR⁴R⁵ | R⁶ |
|---|---|---|---|---|---|
| (Part 1) | | | | | |
| A-1 | H | Me | H | NHCH₂Ph | H |
| A-2 | H | Me | H | NHMe | H |
| A-3 | H | Me | H | NH₂ | H |
| A-4 | H | Me | H | NH₂ | C(=O)NH₂ |
| A-5 | H | Me | H | NHCH₂CH₂-pyrrolidinyl | H |
| A-6 | H | Me | H | NHCH₂CH₂-(3-pyridyl) | H |
| A-7 | H | Me | H | NHCH₂CH₂-morpholinyl | H |
| A-8 | H | Me | H | NHCH₂CH₂NEt₂ | H |
| A-9 | H | Me | H | NHCH₂CH₂-(4-F-phenyl) | H |
| A-10 | H | Me | H | NHCH₂CH₂OMe | H |
| A-11 | H | Me | H | NHCH₂CH₂-(3,5-dimethylisoxazol-4-yl) | H |
| A-12 | H | Me | H | NHCH₂-(4-F-phenyl) | H |
| (Part 2) | | | | | |
| A-13 | H | Me | H | NHCH₂CH₂-(2-oxopyrrolidin-1-yl) | H |
| A-14 | H | Me | H | NHCH₂CH₂-imidazol-1-yl | H |
| A-15 | H | Me | H | NHCH₂-(5-methylisoxazol-3-yl) | H |
| A-16 | H | Me | H | NHCH₂-(2-pyridyl) | H |
| A-17 | H | Me | H | NHCH₂CH(OH)CH₂OH | H |
| A-18 | H | Me | H | N(CH₂Ph)C(=O)NH₂ | C(=O)NH₂ |

Table A-continued
| Compound | R¹ | R² | R³ | NR⁴R⁵ | R⁶ |
|---|---|---|---|---|---|
| A-19 | H | Me | H | (NH-CH₂-thiazol-2-yl) | H |
| A-20 | H | Me | H | (NH-CH₂-thiazol-2-yl) | C(=O)NH₂ |
| A-21 | H | Me | H | (NH-CH₂-5-(CF₃)-pyridin-2-yl) | H |
| A-22 | H | Me | H | (NH-CH₂-6-(CF₃)-pyridin-3-yl) | H |
| A-23 | H | Me | H | (NH-CH₂-6-(CF₃)-pyridin-2-yl) | H |
| A-24 | H | Me | H | (NH-CH₂-4-(CF₃)-pyridin-2-yl) | H |
| A-25 | H | Me | H | (NH-CH₂-3-(CF₃)-pyridin-2-yl) | H |
Among these, preferred compounds are A-1, A-2, A-4, A-15, A-16, A-17, A-19, and A-21. Their full structures are shown below:
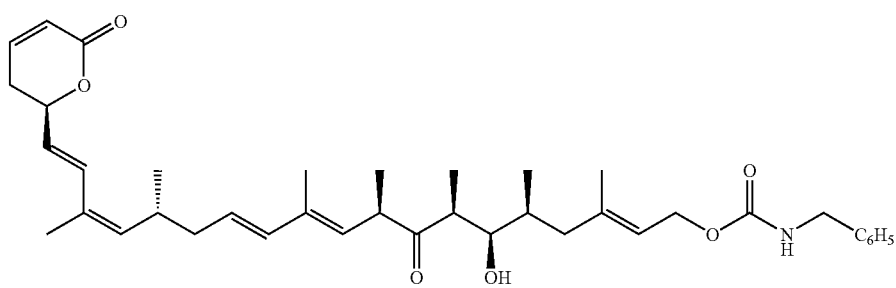
(A-1)
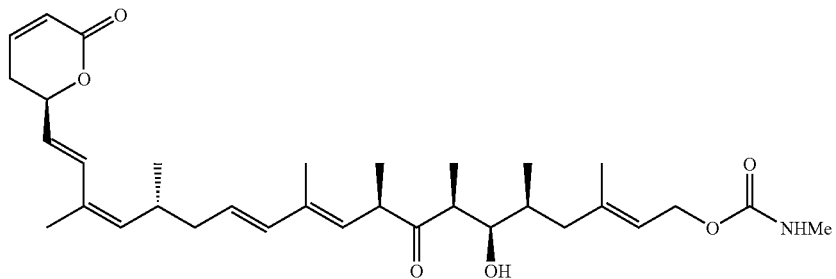
(A-2)
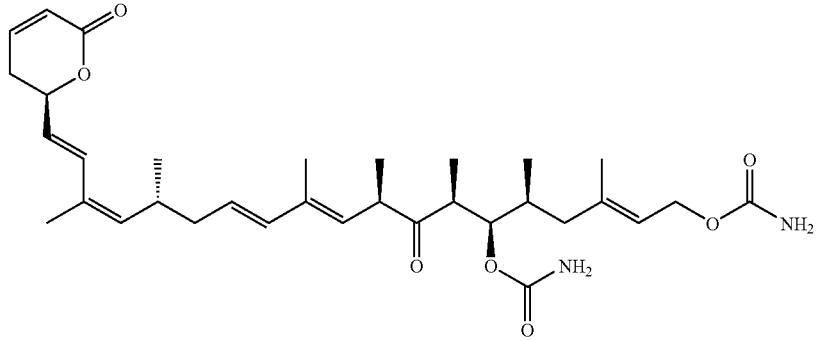
(A-4)

-continued
(A-15)
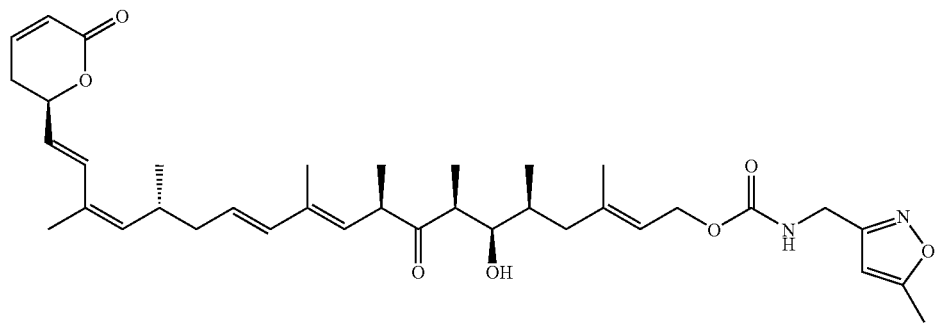
(A-16)
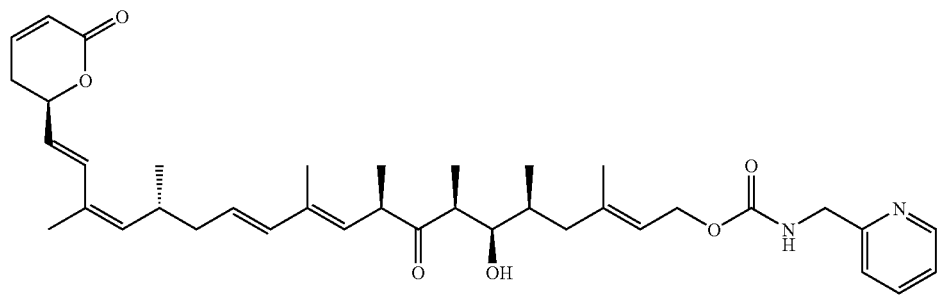
(A-17)
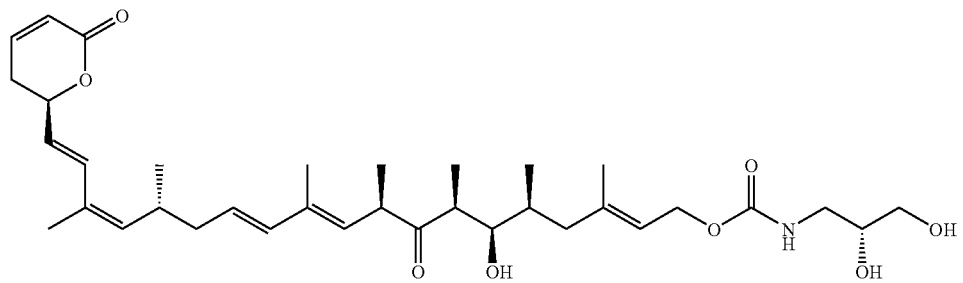
(A-19)
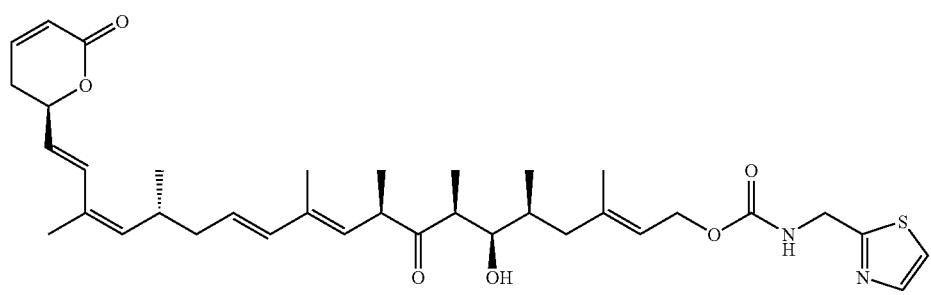
(A-21)
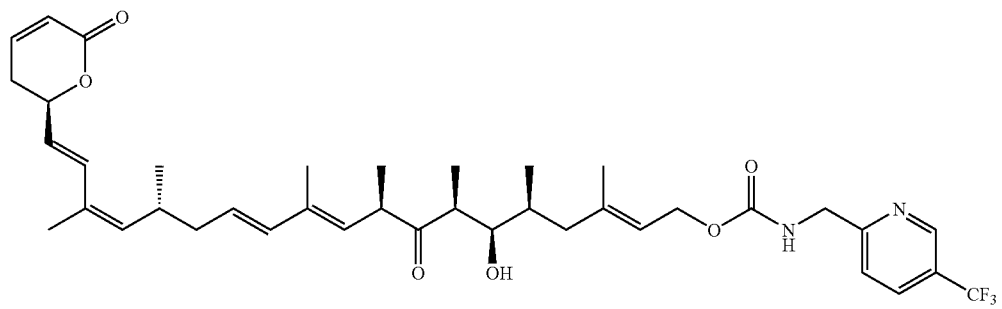

In another preferred embodiment of compounds of formula I-a, the moiety $NR^4R^5$ contains a trifluoromethyl-substituted pyridyl ring and $R^6$ is H. Specific examples of such compounds include:
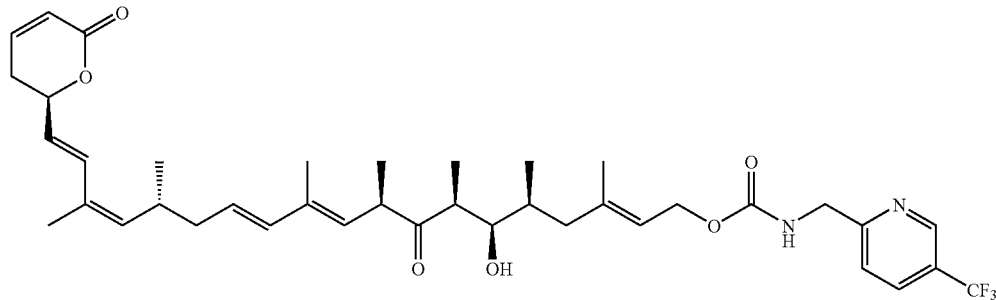
(A-21)
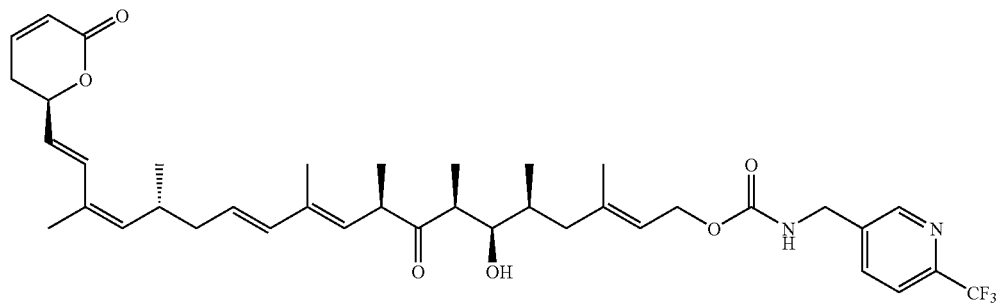
(A-22)
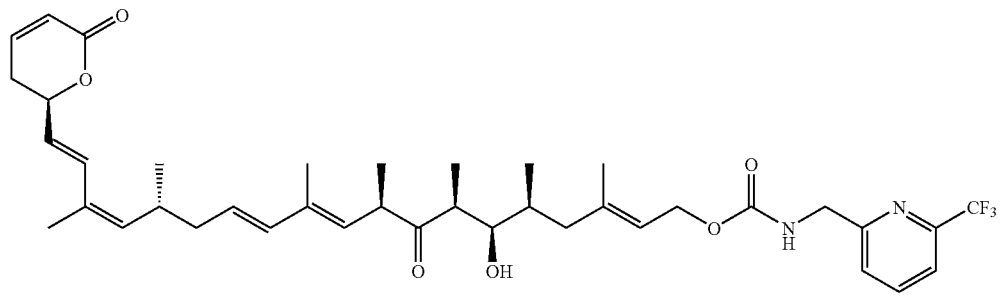
(A-23)
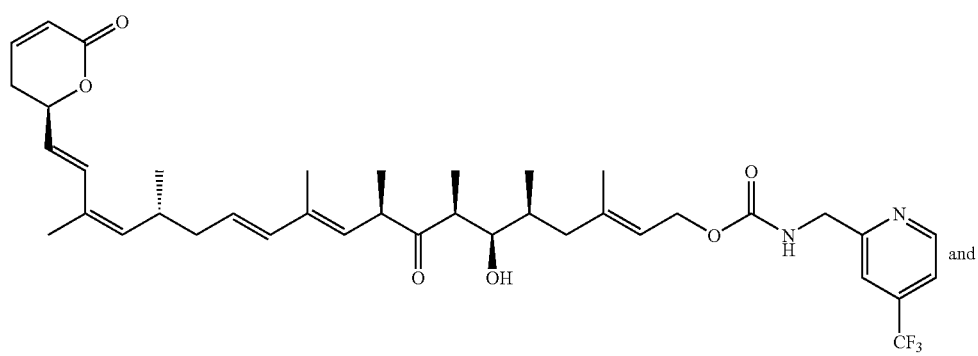
(A-24)
and
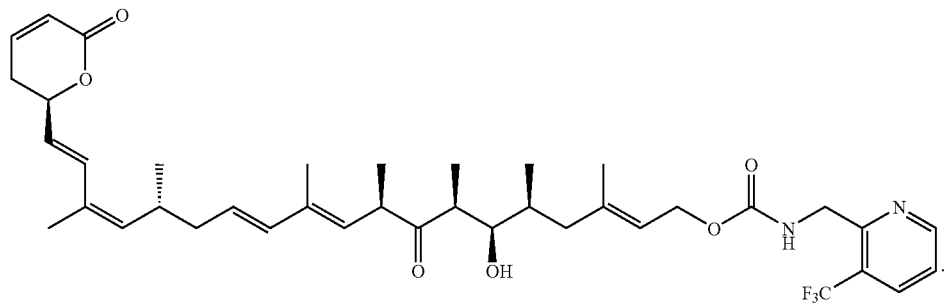
(A-25)

In another preferred embodiment, a compound of this invention has a structure according to formula A-4:

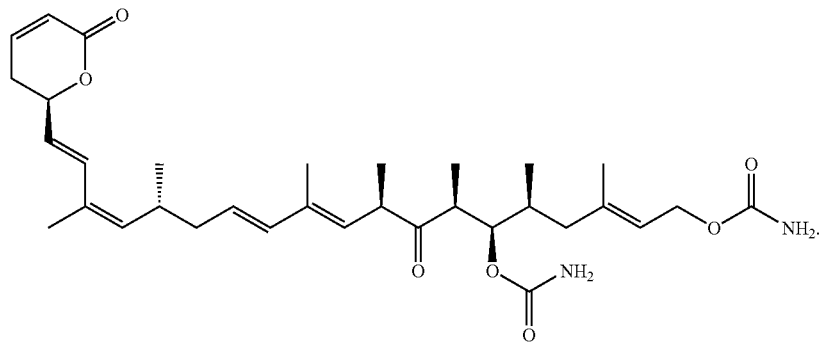

(A-4)

In another embodiment, there is provided a carbamate compound having a structure represented by formula (IV):

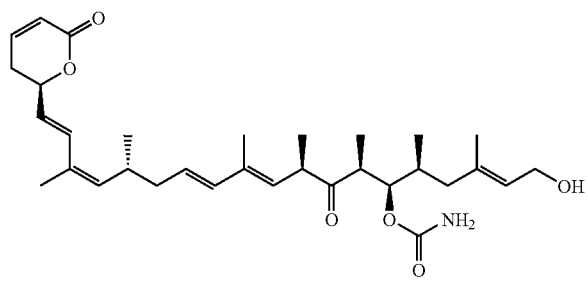

(IV)

A first method for preparing compounds of this invention is shown in FIG. 1. Starting from a C24 alcohol II (where $R^1$, $R^2$, and $R^3$ are as defined above), carbamoylation with an isocyanate O=C=$NR^4$ yields compound I-b (i.e., compound I in which $R^5$ and $R^6$ are both H). The primary alcohol group at C24 is more reactive than the secondary alcohol group at C19, so that carbamoylation occurs essentially exclusively at C24, even under the more forcing conditions where 4-(dimethylamino)pyridine ("DMAP") is added. The method of FIG. 1 is most practical where the isocyanate O=C=$NR^4$ is commercially available.

A second method is shown in FIG. 2. Unlike the method of FIG. 1, this method can yield compounds I in which $R^6$ is H (i.e., compound I-c) or C(=O)$NR^4R^5$ (i.e., compound I-d). Also unlike the method of FIG. 1, this method can afford compounds in which $R^5$ is other than H. Starting again from C24 alcohol II, reaction with 1.0 to 1.2 equivalents of carbonyldiimidazole yields the monoacylimidazole III-a. However, if a larger amount of carbonyldiimidazole (approximately 2.5 equivalents) is employed, the bisacylimidazole compound III-b is formed. Reaction of acylimidazole III-a or III-b with an amine HN$R^4R^5$ yields compound I-c or I-d, respectively.

A third method is shown in FIG. 3. This method is suitable where the moiety $NR^4R^5$ in formula I (whether attached to C24 or C19) is $NH_2$. Reaction of C24 alcohol II with about 1.75 equivalents of trichloroacetylisocyanate followed by treatment with neutral alumina yielded an approximately 1:1 mixture of compounds I-e (i.e., compound I where $R^6$ is H and $NR^4R^5$ is $NH_2$) and I-f (i.e., compound I where $R^6$ is $NR^4R^5$ and each occurrence of $NR^4R^5$ is $NH_2$). If, however, a larger amount (about 5 equivalents) of trichloroacetyliso-cyanate is employed, then only compound I-f is obtained.

A suitable C24 alcohol II is leptolstatin (formerly known as S-59917a), which is biosynthesized by the microorganism *Streptomyces* sp. SAM 1595. Its production, isolation, and characterization is described in Abe et al., *J. Antibiotics* 1993, 46(5), 735-40; Abe et al., JP 05-039283 (1993) (corresponding Chemical Abstract No. 119:137524); and Abe et al., *J. Antibiotics* 1993, 46(5), 728-734; the disclosures of which are incorporated by reference.

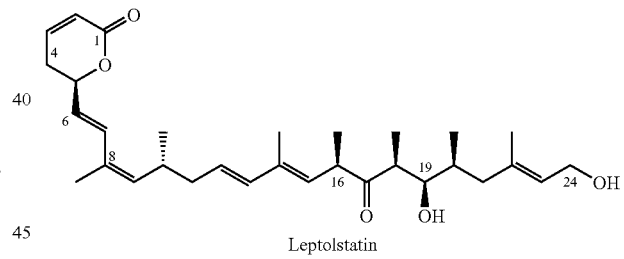

Leptolstatin

Another suitable C24 alcohol II is reductoleptomycin A, whose preparation and isolation from cultures of *Streptomyces* sp. MJ132-NF5 is described in Hosokawa et al., *J. Antibiotics* 1993, 46(4), 676-8, the disclosure of which is incorporated by reference. Structurally, reductoleptomycin A corresponds to leptomycin A with the C24 carboxylic acid group reduced to the alcohol.

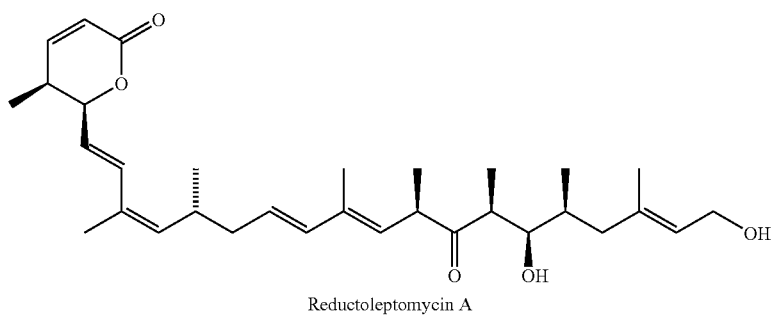

Reductoleptomycin A

The leptomycin B derivative with the C24 carboxylic acid group reduced, analogous to reductoleptomycin A, is another suitable C24 alcohol II that can be employed. Its preparation is described in Kobayashi et al., *Tetrahedron Lett.* 1998, 39(45), 8291-8294, the disclosure of which is incorporated by reference.

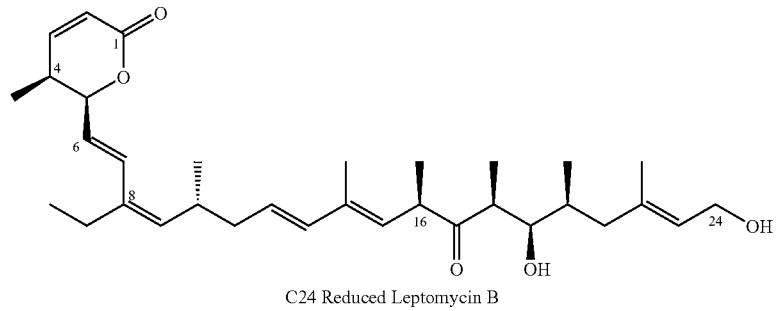

C24 Reduced Leptomycin B

Those skilled in the art will understand that yet other C24 alcohols II can be prepared by the reduction of the C24 carboxylic acid group in other naturally occurring members of the leptomycin family, such as the kazusamycins and the anguinomycins.

Without being bound by theory, it is believed that compounds of this invention function by a mechanism analogous to that of LMB in inhibiting CRM-1 mediated nuclear export processes in the target cancer cells, thus inducing cell cycle arrest and/or apoptosis. The 2,3-dehydro-δ-valerolactone moiety in LMB is a Michael reaction acceptor. LMB has been shown to inhibit CRM1 by forming a Michael adduct with cysteine 529 of yeast CRM1. Kudo et al., *Proc. Nat'l Acad. Sci.* (USA) 1999, 96(3), 9112-9117 (the corresponding cysteine in human CRM1 is at position 528). Ratjadone, another member of the leptomycin family, has been shown to inhibit CRM1 by the same mechanism. Meissner et al., *FEBS Lett.* 2004, 576, 27-30.

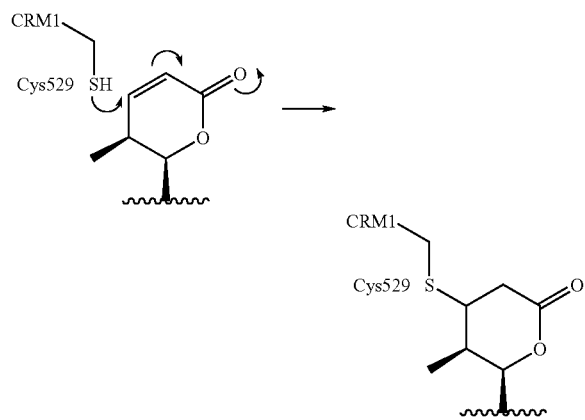

The compounds of this invention retain the Michael acceptor pharmacophore and therefore are expected to function by the same inhibitory mechanism.

Many cancer cells have mutations resulting in the loss of function of the apoptosis-inducing tumor suppressor protein p53. Vousden et al., *Nat. Rev. Cancer* 2002, 2, 594-504. Examples of such cancers include prostate cancer and human papilloma virus (HPV) associated cervical cancer. It has been shown that LMB causes the accumulation of p53 protein in the nucleus of cervical cancer cells. Lane et al., *Proc. Nat'l Acad Sci.* (USA) 2000, 97(15), 8501-8506. LMB has been shown to trap p53 in the nucleus and induce apoptosis in prostate cancer cells. Hence, prostate cancer cells are highly sensitive to LMB. Peehl et al., *Prostate* 2003, 54, 258-267.

Against appropriate types of cancers, compounds of this invention can be used synergistically with other anticancer agents, in particular tyrosine kinase inhibitors such as imatinib (whose mesylate is known by the proprietary name Gleevec®). Some cancers such as chronic myelogenous leukemia (CML) are characterized by expression of the fusion protein Bcr-Abl. While normally Bcr-Abl is not imported into the nucleus, the Bcr-Abl/imatinib complex is imported into the nucleus. If LMB is also present, it prevents the export of Bcr-Abl out of the nucleus. The nuclear-entrapped Bcr-Abl induces apoptosis upon release from its reversible complex with imatinib, resulting in the death of Bcr-Abl positive cells. See, e.g., Vigneri et al., *Nature Medicine* 2001, 7, 228-234; Wang et al., US 2003/0162740 A1 (2003). Thus, the combination of imatinib and a compound of this invention can provide a mechanism for synergistically attacking Bcr-Ab1 positive cancer cells.

Santi et al., US 2005/0203174 A1 (2005), the disclosure of which is incorporated herein by reference, describes various combination therapies involving LMB and a second anticancer agent. Considering the likely common mechanism of action, it is expected that the combination therapies disclosed there can be practiced using a compound of this invention instead of LMB.

Thus, compounds of this invention can be used to inhibit the nuclear export of proteins such as p53, p73, Bcr-Abl, STAT1, (i)ADAR1, Rev, and actin from the nucleus of a cell, by forming a covalent adduct with CRM1 and interfering with the CRM1 mediated export process for such proteins. In one embodiment, the inhibited protein is p53. In another embodiment, the inhibited protein is Bcr-Abl. While a certain variability is to be expected depending on the cell type and the target protein, generally the inhibitory amount used will be in the range of 0.03 to 740 nM, preferably 0.3 to 100 nM, more preferably 0.3 to 20 nM.

Compounds of this invention can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer; breast cancer sarcomas, such as fibrosarcoma, malignant fibrous histiocytoma, embryonal rhabdomyosarcoma, leiomyosarcoma, neurofibrosarcoma, osteosarcoma, synovial sarcoma, liposarcoma, and alveolar soft part sarcoma; leukemias such as acute myelogenous leukemia (AML), acute lymphoblastic leukemia (ALL), and chronic myelogenous leukemia (CML); neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be prostate cancer, leukemia, lung cancer, breast cancer, neuroblastoma, renal cancer, cervical cancer (especially human papilloma virus (HPV)-associated cervical cancer), and colon cancer.

Non-cancer disorders that are characterized by cellular hyperproliferation can also be treated by compounds of this invention. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including idiopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including idiopathic); and eustachean tube diseases (e.g., strictures of all causes including idiopathic). Especially, the non-cancer condition can be plantar warts, cardiac hypertrophy, or cancer cachexia.

Compounds of this invention can be administered in combination with other anti-cancer or cytotoxic agents, including alkylating agents, angiogenesis inhibitors, antime-tabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific anti-cancer or cytotoxic agents include β-lapachone, ansamitocin P3, auristatin, bicalutamide, bleomycin, bortezomib, busulfan, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylamino-ethyl)amino 17-demethoxygeldanamycin (17-DMAG), gemcitabine, hydroxyurea, imatinib, interferons, interleukins, irinotecan, maytansine, methotrexate, mitomycin C, oxaliplatin, paclitaxel, suberoylanilide hydroxamic acid (SAHA), thiotepa, topotecan, trichostatin A, vinblastine, vincristine, vindesine, lenalidomide (Revlimid®), bevacizumab (Avastin®), trastuzumab (Herceptin®), and cetuximab (Erbitux®).

Preferably, compounds of this invention are provided in a purified and isolated form, for example following column chromatography, high-pressure liquid chromatography, recrystallization, or other purification technique. Where particular stereoisomers of compounds of this invention are denoted, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semisolid, or liquefied form. In addition, auxiliary stabilizing, thickening, and coloring agents and perfumes may be used. Preferred modes of administration include intravenously and, in the case of certain indications such a cervical cancer, bladder cancer, or plantar warts, topically.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534,270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 1 mg to about 20 mg per kilogram of body weight per day, corresponding to 70 mg to 1400 mg per patient per day, assuming a 70 kg patient. The compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The practice of this invention can be further understood by reference to the following examples, which are provided by way of illustration and not of limitation.

Example 1

Leptolstatin

*Streptomyces* sp. strain SAM1595 was stored in glycerol (30%, v/v) at −80° C. in vials. One vial was thawed and the contents were transferred into a baffled 250 mL Erlenmeyer shake flask containing 50 mL of L2 medium (soy oil, 60 mL/L; basic yeast, 30 g/L; KCl, 3 g/L; $K_2HPO_4$, 0.2 g/L; $CaCO_3$, 3 g/L). The flask was cultivated at 24° C. for four days in a 2-inch throw incubator. The content of the flask were transferred into a 2.8 L Fembach flask containing 500 mL of L2 medium. The Fembach flask was cultivated at 24° C. for two days in a 2-inch throw incubator. Two-hundred mL of the secondary seed culture was used to inoculate 4 liters of L2 medium in a bioreactor. The conditions of the cultivation were controlled at 24° C., aeration rate of 0.5 v/v/m, dissolved oxygen tension at 30% of saturation using a stir cascade initially set at 600 rpm, and pH at 7.0 using 2.5 N $H_2SO_4$ or 2.5 N NaOH. After seven days of cultivation, 3 L of broth were extracted with 3 L of 100% methanol overnight. The extraction mixture was filtered through a Buchner funnel, and the filter cake was washed with 200 mL of 50:50 methanol: water. All the solvents used in the purification process contained 0.1% (v/v) acetic acid. Leptolstatin was purified from the methanol extract by low-pressure C18 chromatography. A total of 115 mg of leptolstatin was obtained as a yellow oil with an overall recovery yield of 32%.

Example 2

24-Acylimidazole Leptolstatin

This example illustrates the preparation of monoacylimidazole compounds III-a via the scheme of FIG. 2, using leptolstatin as a representative C24 alcohol II.

1,1'-Carbonyldiimidazole (54 mg, 0.3333 mmol, 1.01 eq) was added to leptolstatin (164 mg, 0.3293 mmol, 1 eq) in 1 mL dry acetonitrile. The reaction mixture was stirred at room temperature for 2.5 h and the solvent was removed. The product was purified by silica gel column chromatography (10-50% acetone in hexane gradient) to yield 182 mg of 24-acyhnidazole leptolstatin. MS (m/z): calculated for $C_{35}H_{48}N_2O_6$ 592.765; found 615.427 (M+Na$^+$).

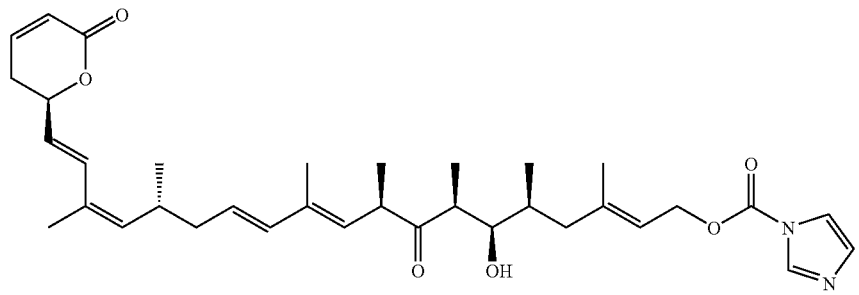

24-Acylimidazole leptolstatin

Example 3

19,24-Bisacylimidazole Leptolstatin

This example illustrates the preparation of bisacylimidazole compounds III-b via the scheme of FIG. 2, using leptolstatin as a representative C24 alcohol II.

1,1'-Carbonyldiimidazole (127 mg, 0.7840 mmol, 2.4 eq) was added to leptolstatin (163 mg, 0.3273 mmol, 1 eq) in 3 mL dry acetonitrile. The reaction mixture was stirred at room temperature overnight and the solvent was removed. The product was purified by silica gel column chromatography (10-50% acetone in hexane gradient) to yield 128 mg of 19,24-bisacylimidazole leptolstatin. MS (m/z): calculated for $C_{39}H_{50}N_4O_7$ 686.4; found 687.5 (M+H$^+$), 709.5 (M+Na$^+$).

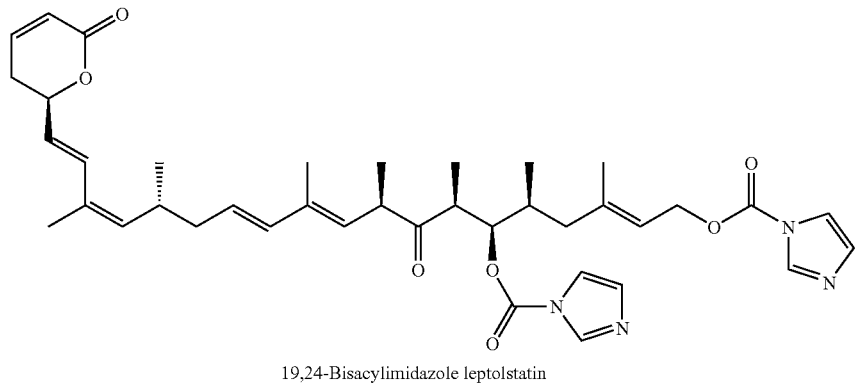
19,24-Bisacylimidazole leptolstatin
Example 3
Compound A-1

This example describes the synthesis of compound A-1 following the scheme of FIG. 1.

Benzylisocyanate (192 μL, 1.5562 mmol, 2.48 eq) and DMAP (115 mg) were added to leptolstatin (312 mg, 0.6265 mmol, 1 eq) in 5 mL dry $CH_2Cl_2$. The reaction mixture was stirred at room temperature for 2.5 h and the solvent was removed. The product was purified by silica gel column chromatography (10-50% acetone in hexane gradient), followed by a C-18 reverse phase MPLC (20-100% acetonitrile in water gradient) to yield 279 mg of compound A-1. MS (m/z): calculated for $C_{39}H_{53}NO_6$ 631.4; found 654.4 ($M+Na^+$). $^{13}C$ NMR (100 MHz, $CDCL_3$), δ (ppm), 215.42, 164.08, 156.72, 144.88, 139.94, 139.00, 138.63, 136.24, 136.34, 130.75, 129.45, 128.57, 128.33, 127.70, 127.41, 127.34, 125.40, 121.50, 121.06, 78.65, 74.09, 61.67, 46.71, 45.61, 44.99, 44.01, 40.70, 33.12, 32.25, 30.01, 20.70, 20.34, 16.16, 15.98, 13.73, 13.06, 12.57. The $^1H$-NMR spectrum of compound A-1 is shown in FIG. 4.

Example 4

Compound A-2

This is another example of a synthesis according to the scheme of FIG. 1.

Methylisocyanate (66 μL, 1.100 mmol, 2.5 eq) and DMAP (40 mg) were added to leptolstatin (219 mg, 0.4398 mmol, 1 eq) in 5 mL dry $CH_2Cl_2$. The reaction mixture was stirred under nitrogen at room temperature for 4 h and the solvent was removed. The product was purified by silica gel column chromatography (5-40% acetone in hexane gradient), followed by a C-18 reverse phase MPLC (20-100% acetonitrile in water gradient) to yield 185 mg of compound A-2. MS (m/z): calculated for $C_{33}H_{49}NO_6$ 555.4; found 578.4 ($M+Na^+$). $^{13}C$ NMR (100 MHz, $CDCL_3$), δ (ppm), 215.54, 164.03, 157.29, 144.70, 139.87, 139.05, 136.29, 135.34, 130.81, 129.47, 128.34, 127.75, 125.40, 121.65, 121.22, 78.66, 74.19, 61.52, 46.49, 45.62, 43.95, 40.73, 33.10, 32.28, 30.08, 27.54, 20.72, 20.36, 16.15, 15.99, 13.92, 13.08, 12.29. The $^1H$-NMR spectrum of compound A-2 is shown in FIG. 5.

Example 5

Compounds A-3 and A-4 (Mixture)

This example describes the synthesis of a mixture of compounds A-3 and A-4, following the scheme of FIG. 3.

Trichloroacetylisocyanate (5 μL, 0.04204 mmol, 1.74 eq) was added to leptolstatin (12 mg, 0.0241 mmol, 1 eq) in 1 mL dry $CH_2Cl_2$. The reaction mixture was stirred at room temperature for 30 min and then loaded directly on a neutral $Al_2O_3$ chromatography column. After 4 hours, the product was eluted with acetone. The solvent was evaporated and the product was purified by silica gel column chromatography (5-60% acetone in hexane gradient) to yield 6 mg of compound A-3 and 6 mg of compound A-4 (MS (m/z): calculated for $C_{33}H_{48}N_2O_7$ 584.346.340; found 607.392 ($M+Na^+$)). MS (m/z) for compound A-3: calculated for $C_{32}H_{47}NO_6$ 541.3; found 564.4 ($M+Na^+$). $^{13}C$ NMR for compound A-3 (100 MHz, $CDCL_3$), δ (ppm), 215.54, 164.05, 156.87, 144.71, 140.25, 139.05, 136.30, 135.34, 130.82, 129.48, 128.33, 127.77, 125.39, 121.65, 120.82, 78.66, 74.19, 61.81, 46.49, 45.63, 43.94, 40.73, 33.09, 32.28, 30.08, 20.72, 20.36, 16.14, 16.00, 13.93, 13.09, 12.28. The $^1H$-NMR spectrum of compound A-3 is shown in FIG. 6. For analytical particulars regarding compound A-4, see the next example.

Example 6

Compound A-4

This example describes the synthesis of compound A-4 by the scheme of FIG. 1, using a limited amount of trichloroacetylisocyanate.

Trichloroacetylisocyanate (73.6 μL, 0.6189 mmol, 5 eq) was added to leptolstatin (74 mg, 0.1237 mmol, 1 eq) in 2 mL dry $CH_2Cl_2$. The reaction mixture was stirred at room temperature for 30 min and then loaded directly on a neutral $Al_2O_3$ chromatography column. After 4 h, the product was eluted with acetone. The solvent was evaporated and the product was purified by silica gel column chromatography (5-60% acetone in hexane gradient) to yield obtain 55 mg of compound A-4. MS (m/z): calculated for $C_{33}H_{48}N_2O_7$ 584.4; found 607.4 ($M+Na^+$). $^{13}C$ NMR (100 MHz, $CDCL_3$), δ (ppm), 211.89 (C17), 164.16 (C1), 157.25, 157.13, 145.02 (C3), 139.36 (22), 139.05 (C9), 136.25 (C14), 135.29 (C13), 130.89 (C7), 129.52 (C8), 128.53 (C15), 127.83 (C12), 125.36 (C6), 121.48 (C2), 121.05 (C23), 78.94 (C5), 76.64 (C19), 61.78 (C24), 46.78 (C18), 45.45 (C16), 44.38 (C21), 40.77 (C11), 32.79 (C20), 32.54 (C10), 30.11 (C4), 20.87 (10 Me), 20.34 (8 Me), 16.05 (16 Me), 15.91 (22 Me), 14.07 (18 Me), 13.13 (14 Me), 12.82 (20 Me). The $^1$H-NMR spectrum of compound A-3 is shown in FIG. 6.

Compound A-4 can also be synthesized as follows: To leptolstatin (17.78 g, 35.70 mmol, 1 eq) in 360 mL dry $CH_2Cl_2$, was added trichloroacetylisocyanate (10.57 mL, 89.25 mmol, 2.5 eq). The reaction mixture was stirred at room temperature for 30 min. The $CH_2Cl_2$ was removed with a rotary evaporator and methanol (360 mL) was added followed by the addition of $NaHCO_3$ (89 g). The reaction mixture was stirred at room temperature for 2.5 hours. The solid was removed by filtration and the solvent was removed with a rotary evaporator. The product was purified by silica gel column chromatography ((5-60% acetone in hexane gradient) to yield 16.5 g of compound A4.

Example 7

Compound A-5

Compound A-5 was synthesized according to the scheme of FIG. 2, via an intermediate III-a N-(2-Aminoethyl)pyrrolidine (6.8 µL, 0.05374 mmol, 4.4 eq) and acetic acid (3 µL, 0.053 mmol, 4.3 eq) were added to 24-acylimidazole leptolstatin (7.3 mg, 0.01233 mmol, 1 eq) in 1.5 mL dry tetrahydrofuran. The reaction mixture was stirred at room temperature for 5 h. The reaction mixture was directly loaded on a silica gel chromatography column for purification (2-6% methanol in $CH_2Cl_2$ gradient) to yield 7.1 mg of compound A-5. MS (m/z): calculated for $C_{38}H_{58}N_2O_6$ 638.4; found 639.4 (M+H$^+$). $^{13}$C NMR (100 MHz, $CDCL_3$), δ (ppm), 215.52, 164.04, 156.78, 144.73, 139.76, 139.05, 136.27, 135.35, 130.80, 129.46, 128.34, 127.73, 125.40, 121.63, 121.20, 78.67, 74.07, 61.63, 55.22, 54.03, 46.54, 45.62, 43.95, 40.72, 38.86, 33.08, 32.28, 30.07, 29.68, 20.71, 20.36, 16.16, 15.98, 13.91, 13.08, 12.36. The $^1$H-NMR spectrum of compound A-5 is shown in FIG. 8.

In the subsequent examples, syntheses that were performed analogously to prior examples are so noted for the sake of brevity. Unless noted otherwise, the amines used in such syntheses were commercially available, either as the free base or the hydrochloride. If obtained as the hydrochloride, the free base generated by dissolving the hydrochloride in methanol, treatment with excess solid sodium carbonate, filtration, removal of the methanol by rotary evaporator, and drying under high vacuum.

Example 8

Compound A-6

Compound A-6 was prepared analogously to compound A-5, using 2-(pyridin-3-yl)ethanamine. MS (m/z): calculated for $C_{39}H_{54}N_2O_6$ 646.4; found 647.4 (M+H$^+$). $^{13}$C NMR (100 MHz, $CDCL_3$), δ (ppm), 215.44, 164.02, 156.52, 150.14, 147.85, 144.69, 140.12, 139.05, 136.38, 136.24 135.39, 134.33, 130.77, 129.46, 128.340, 127.68, 125.41, 123.54, 121.65, 121.00, 78.64, 73.54, 61.54, 46.89, 45.70, 44.05, 41.84, 40.73, 33.37, 33.06, 32.28, 30.08, 20.70, 20.37, 16.18, 15.92, 13.88, 13.09, 12.82. The $^1$H-NMR spectrum of compound A-6 is shown in FIG. 9.

Example 9

Compound A-7

Compound A-7 was prepared analogously to compound A-5, using 2-morpho-linoethanamine. MS (m/z): calculated for $C_{38}H_{58}N_2O_7$ 654.4; found 655.4 (M+H$^+$). $^{13}$C NMR (100 MHz, $CDCL_3$), δ (ppm), 215.45, 164.02, 156.62, 144.70, 139.95, 139.03, 136.29, 135.34, 130.81, 129.48, 128.33, 127.75, 125.40, 121.65, 121.15, 78.65, 74.11, 66.88, 61.55, 57.44, 53.32, 46.56, 45.61, 43.98, 40.73, 37.19, 33.10, 32.29, 30.08, 20.72, 20.37, 16.17, 16.01, 13.86, 13.08, 12.41. The $^1$H-NMR spectrum of compound A-7 is shown in FIG. 10.

Example 10

Compound A-8

Compound A-8 was prepared analogously to compound A-5, using $N^1,N^1$-diethylethane-1,2-diamine. MS (m/z): calculated for $C_{38}H_{60}N_2O_6$ 640.5; found 641.5 (M+H$^+$). $^{13}$C NMR (100 MHz, $CDCL_3$), δ (ppm), 215.52, 164.02, 156.74, 144.70, 139.70, 139.04, 136.27, 135.35, 130.80, 129.46, 128.34, 127.74, 125.40, 121.45, 121.31, 78.66, 74.18, 61.46, 51.87, 46.75, 46.50, 45.61, 43.96, 40.72, 38.41, 33.09, 32.28, 30.07, 20.71, 20.36, 16.17, 15.98, 13.91, 13.08, 12.30, 11.51. The $^1$H-NMR spectrum of compound A-8 is shown in FIG. 11.

Example 11

Compound A-9

Figure 12:
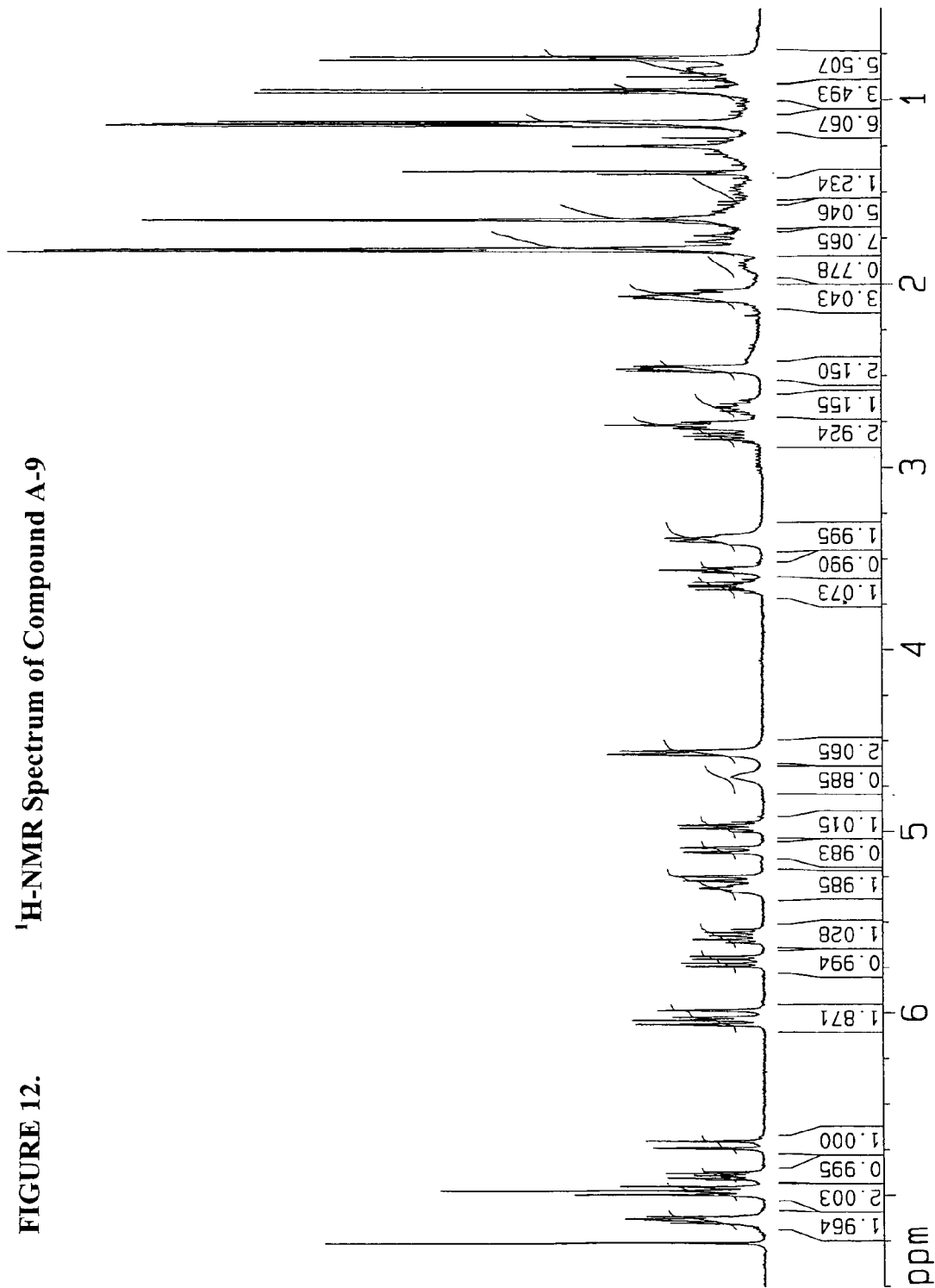

2-(4-Fluorophenyl)ethylamine (13 µL, 0.09923 mmol, 4.02 eq) and acetic acid (3 µL, 0.053 mmol, 2.15 eq) were added to 24-acylimidazole leptolstatin (14.6 mg, 0.02466 mmol, 1 eq) in 1 mL dry tetrahydrofuran. The reaction mixture was stirred at room temperature for 3 h. The reaction mixture was directly loaded on a silica gel chromatography column for purification (5-40% acetone in hexane gradient) to yield 9.6 mg of compound A-9. MS (m/z): calculated for $C_{40}H_{54}NO_6$ 663.4; found 686.4 (M+Na$^+$). $^{13}$C NMR (100 MHz, $CDCL_3$), δ (ppm), 215.49, 164.03, 162.84, 160.41, 156.55, 144.71, 140.00, 139.03, 136.29, 135.34, 134.41, 130.80, 130.20, 130.13, 129.48, 128.33, 127.75, 125.40, 121.64, 121.08, 115.48, 115.26, 78.65, 74.16, 61.54, 46.51, 45.61, 43.94, 42.23, 40.73, 36.63, 35.38, 33.09, 32.28, 30.07, 20.72, 20.36, 16.16, 16.00, 13.87, 13.08, 12.34. The $^1$H-NMR spectrum of compound A-9 is shown in FIG. 12.

Example 12

Compound A-10

Compound A-10 was prepared analogously to compound A-9, using 2-methoxyethanamine. MS (m/z): calculated for $C_{35}H_{53}NO_7$ 599.4; found 622.4 (M+Na$^+$). $^{13}$C NMR (100 MHz, $CDCL_3$), δ (ppm), 215.52, 164.02, 156.67, 144.69, 139.88, 139.04, 136.28, 135.34, 130.81, 129.47, 128.34, 127.75, 125.40, 121.66, 121.15, 78.66, 74.19, 71.43, 61.57, 58.74, 46.49, 45.61, 43.94, 40.73, 33.09, 32.29, 30.07, 29.68, 20.71, 20.36, 16.16, 15.99, 13.90, 13.08, 12.28. The $^1$H-NMR spectrum of compound A-10 is shown in FIG. 13.

Example 13

Compound A-11

Figure 14:
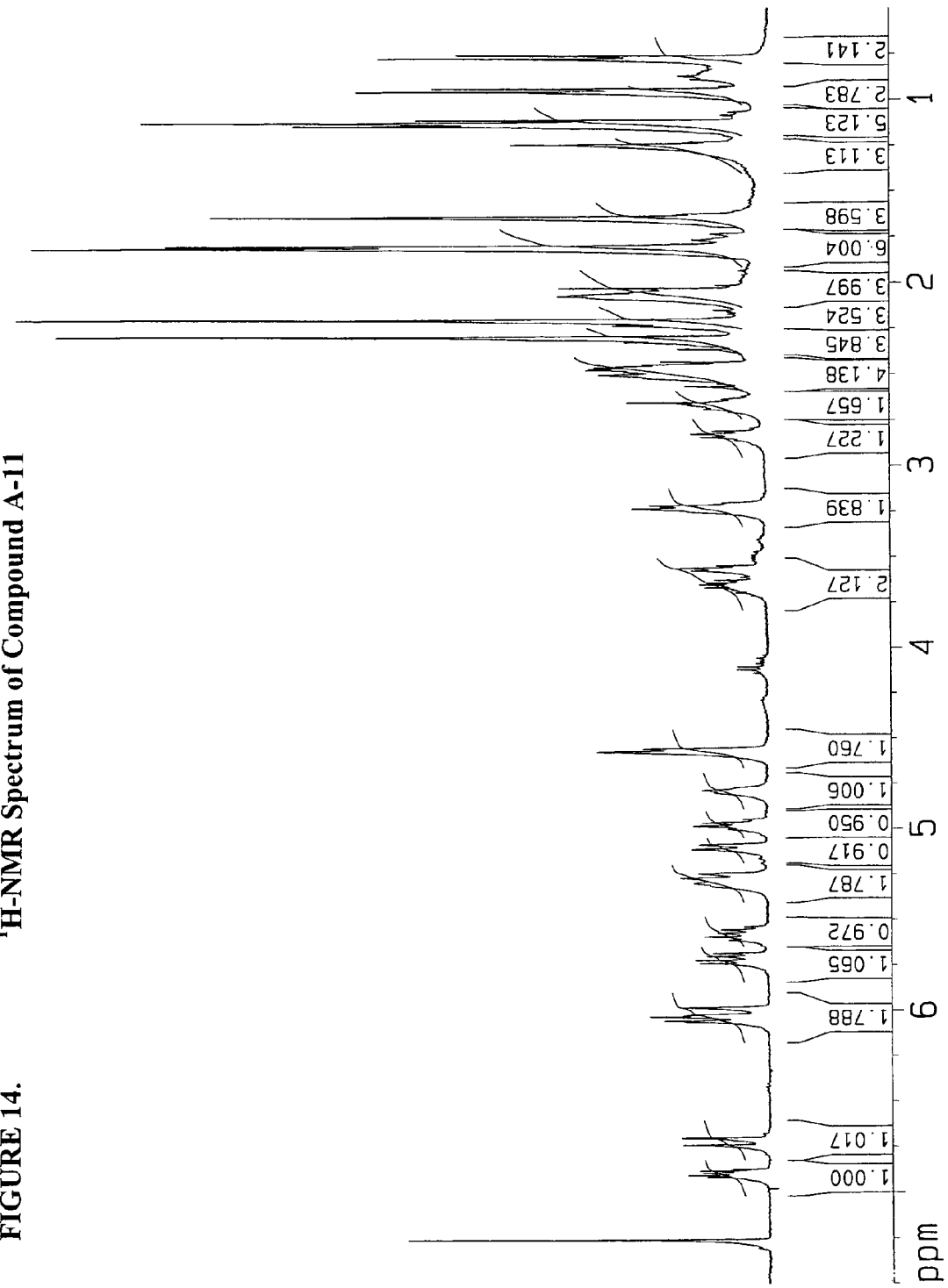

Compound A-11 was prepared analogously to compound A-9, using 2-(3,5-dimethylisoxazol-4-yl)ethanamine. MS (m/z): calculated for $C_{39}H_{56}N_2O_7$ 664.4; found 665.4 (M+H$^+$), 687.4 (M+Na$^+$). $^{13}$C NMR (100 MHz, CDCL$_3$), δ (ppm), 215.45, 165.85, 164.05, 159.62, 156.58, 144.73, 140.12, 139.03, 136.28, 135.35, 130.80, 129.49, 128.34, 127.75, 125.40, 121.63, 120.95, 110.57, 78.65, 74.08, 61.62, 46.58, 45.62, 43.95, 40.73, 40.61, 33.08, 32.28, 30.08, 22.28, 20.72, 20.36, 16.16, 15.98, 13.86, 13.09, 12.42, 10.90, 10.13. The $^1$H-NMR spectrum of compound A-11 is shown in FIG. 14.

Example 14

Compound A-12

Figure 15:
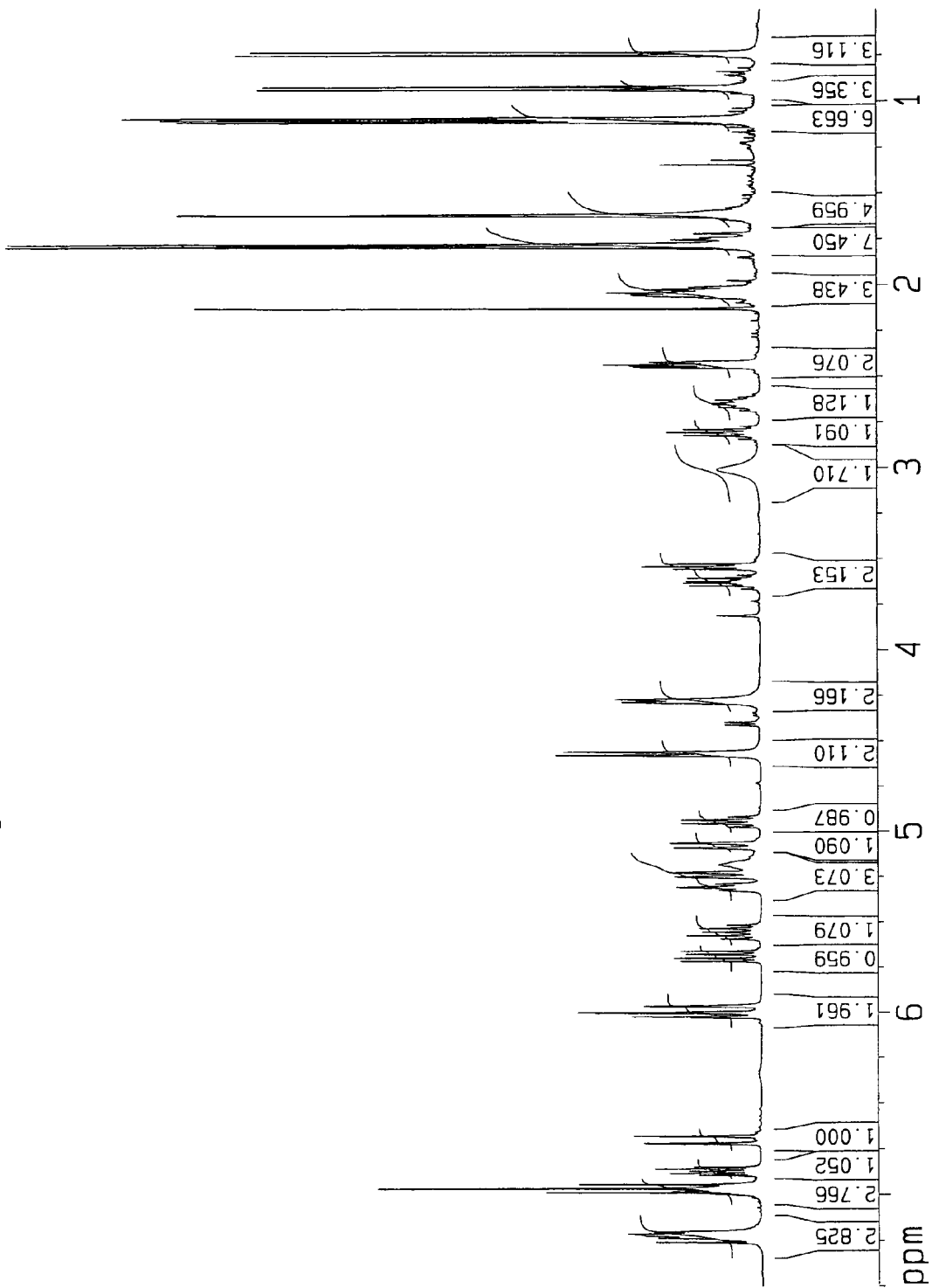

Compound A-12 was prepared analogously to compound A-9, using (4-fluoro-phenyl)methanamine. MS (m/z): calculated for $C_{39}H_{52}FNO_6$ 649.4; found 672.4 (M+Na$^+$). $^{13}$C NMR (100 MHz, CDCL$_3$), δ (ppm), 215.44, 164.09, 163.30, 160.86, 156.69, 144.84, 140.06, 139.02, 136.26, 135.33, 134.46, 130.78, 129.46, 129.15, 129.07, 128.32, 127.73, 125.38, 121.53, 120.98, 115.48, 115.26, 78.66, 74.08, 61.73, 46.66, 45.61, 44.28, 43.98, 40.71, 33.11, 32.26, 30.03, 20.70, 20.34, 16.15, 15.98, 13.76, 13.06, 12.51. The $^1$H-NMR spectrum of compound A-12 is shown in FIG. 15.

Example 15

Compound A-13

Compound A-13 was prepared in a similar way as that for compound A-5, using 1-(2-aminoethyl)pyrrolidin-2-one. MS (m/z): 675.4 (M+Na$^+$). $^{13}$C NMR (100 MHz, CDCL$_3$), δ (ppm), 215.42, 176.08, 164.03, 156.88, 144.73, 139.77, 139.01, 136.21, 135.35, 130.74, 129.43, 128.36, 127.66, 125.38, 121.59, 121.12, 78.63, 73.69, 61.55, 47.59, 46.77, 45.61, 44.03, 42.51, 40.69, 38.95, 33.00, 32.24, 30.84, 20.67, 20.33, 18.03, 16.03, 16.15, 15.87, 13.78, 13.05, 12.68.

Example 16

Compound A-14

To 24-acylimidazolide leptolstatin (190 mg, 0.3204 mmol, 1 eq) in 5 mL dry tetrahydroftiran, was added 2-(imidazol-1-yl)-ethylamine (142 mg, 1.281 mmol, 4 eq) and acetic acid (90.7 µL, 1.6023 mmol, 5 eq). The reaction mixture was stirred at room temperature for 5 hours. The reaction mixture was directly loaded on a silica gel column for purification (2-6% methanol in dichloromethane) to obtain 102 mg of Compound A-14. MS (m/z): found 636.4 (M+H$^+$). $^{13}$C NMR (100 MHz, CDCL$_3$), δ (ppm), 215.40, 164.09, 156.72, 144.90, 140.23, 139.01, 137.41, 136.12, 135.41, 130.70, 129.40, 128.42, 127.55, 125.38, 121.48, 120.80, 118.86, 78.65, 72.93, 61.71, 47.41, 46.43, 45.74, 44.19, 41.68, 40.68, 33.09, 32.22, 30.01, 20.64, 20.33, 16.20, 15.86, 13.65, 13.51, 13.04.

Example 17

Compound A-15

Compound A-15 was prepared in a similar fashion as that for Compound A-14, using (5-methylisoxazol-3-yl)methanamine. MS (m/z): 659.4 (M+Na$^+$). $^{13}$C NMR (100 MHz, CDCL$_3$), δ (ppm), 215.41, 169.88, 164.06, 161.62, 156.65, 144.83, 140.15, 138.99, 136.25, 135.32, 130.75, 129.45, 128.31, 127.71, 125.40, 121.54, 120.84, 100.85, 78.64, 74.04, 61.91, 46.67, 45.60, 43.98, 40.70, 36.91, 33.09, 32.24, 30.03, 20.69, 20.34, 16.14, 15.97, 13.75, 13.06, 12.53, 12.21.

Example 18

Compound A-16

Compound A-16 was prepared in a similar fashion as that for Compound A-14, using pyridin-2-ylmethanamine. MS (m/z): 655.4 (M+Na$^+$). $^{13}$C NMR (100 MHz, CDCL$_3$), δ (ppm), 215.36, 164.02, 157.22, 156.78, 149.04, 144.82, 139.85, 138.98, 136.71, 136.20, 135.33, 130.72, 129.42, 128.34, 127.67, 125.40, 122.25, 121.63, 121.51, 121.08, 78.62, 74.05, 61.70, 46.74, 46.03, 45.59, 44.03, 40.69, 33.12, 32.23, 30.01, 20.68, 20.33, 16.15, 15.96, 13.71, 13.05, 12.60.

Example 19

Compound A-17

Compound A-17 was prepared in a similar way as that for compound A-5, using (R)-3-aminopropane-1,2-diol, and except the solvent used was THF/DMF (1 mL:1 mL). MS (m/z): 638.4 (M+H$^+$). $^{13}$C NMR (100 MHz, CDCL$_3$), δ (ppm), 215.49, 164.26, 157.96, 145.00, 140.15, 139.06, 136.30, 135.34, 130.84, 129.45, 128.27, 127.72, 125.32, 121.51, 120.91, 78.75, 73.57, 71.17, 63.75, 61.96, 47.00, 45.71, 44.10, 43.27, 40.71, 33.10, 32.27, 30.04, 20.71, 20.35, 16.16, 15.96, 13.65, 13.08, 13.08.

Example 20

Compound A-18

Compound A-18 was prepared in a similar way as that for compound A4. In this case compound A-1 was used as starting material, reacting with trichloroacetylisocyanate (2.5 eq). MS (m/z): 740.4 (M+Na$^+$). $^{13}$C NMR (100 MHz, CDCL$_3$), δ (ppm), 211.75, 164.08, 156.80, 155.88, 155.41, 144.86, 141.40, 139.00, 138.16, 136.30, 135.26, 130.87, 129.52, 128.51, 128.24 (2x), 127.85 (3x), 127.11, 125.33, 121.55, 119.59, 78.90, 76.48, 63.61, 46.77, 46.64, 45.38, 44.38, 40.76, 32.67, 32.53, 30.13, 20.84, 20.35, 16.02, 15.98, 14.19, 13.15, 12.82.

Example 21

Compound A-19

Compound A-19 was prepared in a similar way as that for compound A-5, using thiazol-2-ylmethanamine as the amine. MS (m/z): 661.3 (M+Na$^+$). $^{13}$C NMR (100 MHz, CDCL$_3$), δ (ppm), 215.28, 168.32, 163.97, 156.47, 144.74, 142.33, 140.11, 138.89, 136.13, 135.23, 130.65, 129.34, 128.23, 127.59, 125.28, 121.42, 120.70, 119.23, 78.54, 73.88, 61.93, 46.65, 45.50, 43.92, 42.39, 40.59, 33.00, 32.14, 29.92, 20.59, 20.24, 16.06, 15.88, 13.62, 12.96, 12.55.

Example 22

Compound A-20

Compound A-20 was prepared in a similar way as that for compound A-4. In this case compound A-19 was used as starting material, reacting with trichloroacetylisocyanate (1.2 eq). MS (m/z): 704.3 (M+Na$^+$). $^1$H NMR (400 MHz, CDCL$_3$), δ (ppm), 7.70 (d, J=3.2 Hz, 1H), 7.28 (d, J=3.2 Hz, 1H), 6.91 (dt, J=9.6, 4.4 Hz, 1H), 6.69 (d, J=15.6 Hz, 1H), 6.05 (d, J=9.6 Hz, 1H), 6.02 (d, J=15.6 Hz, 1H), 5.72 (dd, J=15.6, 7.2 Hz, 1H), 5.57 (dt, J=15.6, 6.8 Hz, 1H), 5.49 (br, 1H), 5.31 (t, J=6.4 Hz, 1H), 5.26 (d, J=10 Hz, 1H), 5.09 (d, J=9.6 Hz, 1H), 5.01 (dd, J=8.8, 2 Hz, 1H), 4.95 (q-like, J=7.6 Hz, 1H), 4.72 (br, 2H), 4.68 (d, J=6 Hz, 2H), 4.63 (m, 2H), 3.66 (m, 1H), 2.93 (m, 1H), 2.65 (m, 1H), 2.46 (m, 2H), 2.06 (m, 3H), 1.83 (s, 3H), 1.82 (s, 3H), 1.66 (m, 1H), 1.64 (s, 3H), 1.13 (d, J=6.8 Hz, 3H), 1.10 (d, J=6.4 Hz, 3H), 0.96 (d, J=6.4 Hz, 3H), 0.67 (d, J=6.4 Hz, 3H).

Example 23

Compound A-21

Compound A-21 was prepared in a similar fashion as that for Compound A-14, using (5-(trifluoromethyl)pyridin-2-yl)methanamine. MS (m/z): 701.4 (M+H$^+$). $^{13}$C NMR (100 MHz, CDCL$_3$), δ (ppm), 215.42, 164.05, 161.48, 156.79, 146.08 (d, J=4 Hz), 144.78, 140.18, 139.01, 136.27, 135.32, 133.86 (d, J=3 Hz) 130.78, 129.46, 128.31, 127.73, 125.37, 125.32 (q, J=66 Hz), 121.57, 121.30, 120.88, 78.65, 74.04, 61.92, 46.64, 46.01, 45.61, 43.98, 40.71, 33.11, 32.26, 30.04, 20.69, 20.33, 16.14, 15.99, 13.77, 13.06, 12.49.

(5-(Trifluoromethyl)pyridin-2-yl)methanamine (VI) was prepared as follows: Sodium bicarbonate (0.25 g) and palladium on carbon (0.5 g, 50% wet, 10% Pd/C) were added to a methanolic solution of the hydrochloride chloride salt of (3-chloro-5-(trifluoro-methyl)pyridin-2-yl)methanamine (V) (0.5 g in 50 mL methanol). The mixture was hydrogenated under a hydrogen balloon over 3 h. The reaction mixture was filtered, and evaporated in vacuo. The residue was re-dissolved in methanol (5 mL), re-filtered, and re-evaporated to give crude product (VI) (0.33 g). $^1$H-NMR (CD$_3$OD, 400 MHz): δ 8.92 (s, 1H), 8.16 (d, J=8.2 Hz, 1H), 7.66 (d, J=8.2 Hz, 1H), 4.35 (s, 2H).

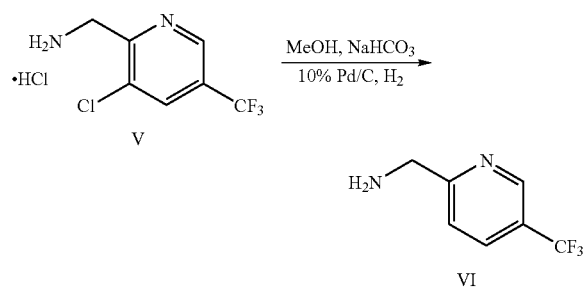

Example 24

Compound A-22

Compound A-22 was prepared in a similar fashion as that for Compound A-14, using (6-(trifluoromethyl)pyridin-3-yl)methanamine. MS (m/z): 723.4 (M+Na$^+$). $^{13}$C NMR (100 MHz, CDCL$_3$), δ (ppm), 215.42, 164.07, 156.75, 149.08, 147.00 (q, J=34.5 Hz), 144.81, 140.40, 138.99, 137.79, 136.39, 136.25, 135.28, 130.77, 129.44, 128.25, 127.70, 125.31, 121.49, 120.65, 120.27, 78.63, 73.97, 62.00, 46.62, 45.59, 43.91, 42.09, 40.68, 33.07, 32.22, 30.01, 20.66, 20.29, 16.09, 15.95, 13.76, 13.02, 12.45.

Example 25

Compound A-23

Compound A-23 was prepared in a similar fashion as that for Compound A-14, using (6-(trifluoromethyl)pyridin-2-yl)methanamine. MS (m/z): 723.4 (M+Na$^+$). $^{13}$C NMR (100 MHz, CDCL$_3$), δ (ppm), 215.46, 164.02, 158.33, 156.72, 147.57 (q, J=35 Hz), 144.73, 140.18, 138.98, 138.04, 136.25, 135.29, 130.76, 129.43, 128.28, 127.71, 125.36, 124.46, 121.55, 120.88, 118.93, 78.62, 74.13, 61.86, 46.51, 45.80, 45.57, 43.91, 40.68, 33.07, 32.23, 30.01, 20.66, 20.30, 16.10, 15.96, 13.82, 13.03, 12.30.

Example 26

Compound A-24

Compound A-24 was prepared in a similar fashion as that for Compound A-14, using (4-(trifluoromethyl)pyridin-2-yl)methanamine. MS (m/z): 701.4 (M+H$^+$). $^{13}$C NMR (100 MHz, CDCL$_3$), δ (ppm), 215.45, 164.04, 159.25, 156.76, 150.17, 144.77, 140.19, 139.01, 138.97 (q, J=68 Hz), 136.25, 135.33, 130.77, 129.45, 128.32, 127.72, 125.38, 121.57, 120.88, 117.91, 117.17, 78.65, 74.09, 61.93, 46.62, 46.05, 45.61, 43.96, 40.70, 33.11, 32.26, 30.04, 20.68, 20.33, 16.14, 15.98, 13.78, 13.05, 12.43.

Example 27

Compound A-25

Compound A-25 was prepared in a similar fashion as that for Compound A-14, using (3-(trifluoromethyl)pyridin-2-yl)methanamine. MS (m/z): 723.4 (M+Na$^+$). $^{13}$C NMR (100 MHz, CDCL$_3$), δ (ppm), 215.53, 164.02, 156.55, 154.22, 151.50, 144.72, 139.92, 139.03, 136.28, 135.34, 134.22, 134.17, 130.80, 129.45, 128.34, 127.74, 125.40, 124.36, 124.04, 123.71, 123.38, 122.14, 121.87, 121.62, 121.15, 78.66, 74.21, 61.77, 46.50, 45.61, 43.96, 43.07, 40.71, 33.10, 32.27, 30.05, 20.69, 20.34, 16.15, 16.00, 13.90, 13.07, 12.27.

Example 28

Compound IV

Trichloroacetylisocyanate (125 μL, 1.054 mmol, 2.5 eq) was added to 24-acylimidazolide leptolstatin (250 mg, 0.4216 mmol, 1 eq) in 3 mL of CH$_2$Cl$_2$. The reaction mixture was stirred at room temperature for 30 min and then loaded on a neutral Al$_2$O$_3$ column and kept on the column over night. The product was eluted from the column with methanol and purified by silica gel column chromatography (3-4% MeOH in $CH_2Cl_2$ gradient). Compound IV (100 mg) product was obtained. MS (m/z): 564.4 (M+Na+). $^{13}C$ NMR (100 MHz, $CDCL_3$), δ (ppm), 211.80, 164.14, 157.13, 144.95, 139.05, 136.89, 136.38, 135.26, 130.95, 129.5, 128.52, 127.93, 126.15, 125.31, 121.54, 79.02, 75.52, 59.13, 46.93, 45.39, 44.73, 40.80, 32.65, 32.52, 30.15, 20.93, 20.36, 15.93, 15.50, 14.27, 13.29, 13.19.

Example 29

Nuclear Export Block

The nuclear export blocking capability of compounds of this invention was evaluated as follows:

$1-5\times10^4$ cells were seeded onto 12 mm glass coverslips or wells of a chamber slide (for example, Lab-Tek #177445). Cells were grown overnight at 37° C. to allow cells to attach to the surface. Media was removed and replaced with media containing the desired test compound and incubated the required time period (typically 1 h). For recovery experiments, cells were washed with PBS or media and incubated in media without test compound for the desired recovery periods (typically 8, 24, or 48 h). The media was removed and coverslips/wells were washed with PBS pH 7.4 for 1 minute. Coverslips or slides were fixed with 3.7% formaldehyde in PBS for 20 minutes at room temperature, washed three times in PBS, and stained for the CRM1 substrate RanBP1.

Coverslips or chamber slides were permeabilized and blocked in 10% donkey serum, 0.1% Triton X-100 in PBS for 30 minutes at room temperature. Primary antibodies were diluted in PBS and incubated for 1 hour at room temperature: goat-anti-RanBP1 (Santa Cruz Biotechnology, sc-1160; 1:50 dilution) and mouse-anti-tubulin (Sigma, T9026; 1:400). Cells were washed 3×5 minutes in PBS. Secondary antibodies donkey-anti-goat Cy3 (705-165-147, Jackson Immunoresearch) and donkey anti-mouse FITC (715-095-150, Jackson Immunoresearch) were diluted 1:200 in PBS and incubated for 1 hour at room temperature. Secondary antibody was removed and cells were stained with a nuclear dye such as DAPI (Sigma, D8417; 2.5 ug/mL in PBS) or Hoechst 33342 (Molecular Probes, H3570; 100 ng/mL in PBS) for 5 minutes at room temperature. Cells were washed 3×5 minutes in PBS and coverslips were mounted with FluorSave (EMD Biosciences, 80058-108). Nuclear (N) or cytoplasmic (C) localization of RanBP1 was examined using a 40× objective on a Zeiss Axiovert 200 inverted epiflourescence microscope. Nuclear localization (N>C) was confirmed after the initial drugging period. Recovery was defined as follows: fast recovery (C≧N at 8 h), moderate recovery (C≧N at 24 h), or slow recovery (N>C at 24 h).

The results are presented in Table B, with comparative data for the natural products leptomycin A, leptomycin B, and leptolstatin included. As can be seen from the results, the duration of nuclear export block is variable, depending on the test compound.

TABLE B

| Compound | Nuclear Export Block * |
|---|---|
| Leptomycin A | Fast recovery |
| Leptomycin B | Slow recovery |
| Leptolstatin | Slow recovery |
| A-1 | Slow recovery |
| A-2 | Slow recovery |
| A-4 | Moderate recovery |
| A-6 | Slow recovery |

Example 30

Biological Activity

The biological activity of compounds of this invention was evaluated by measuring their inhibitory effect on the proliferation of various tumor cell lines. Results, including comparative ones for leptomycin A, leptomycin B, and leptolstatin, are tabulated in Table C. HCT-116 is a human colon cancer cell line. LNCap is a human prostate cancer cell line. SiHa is an HPV-16 positive human cervical cancer line.

TABLE C

| Compound | Exposure time to compound (h) | Cancer Cell Line ($IC_{50}$, nM) | | |
|---|---|---|---|---|
| | | HCT-116 | LNCap | SiHa |
| Leptomycin A | 1 | 19 | — | — |
| | 72 | 1.4 | — | 0.5 |
| Leptomycin B | 1 | 4.3 | 3.3 | 2.1 |
| | 72 | 0.32 | 0.3 | 0.4 |
| Leptolstatin | 1 | 5.5 | — | 1.6 |
| | 72 | 0.49 | — | 0.45 |
| A-1 | 1 | 14.9 | 4.7 | 3.6 |
| | 72 | 3.3 | 1.8 | 1.1 |
| A-2 | 1 | 3.7 | 2.7 | 1.2 |
| | 72 | 0.7 | 0.4 | 0.4 |
| A-3 | 1 | 4.6 | 2.5 | 1.8 |
| | 72 | 0.9 | 0.5 | 0.4 |
| A-4 | 1 | 13.1 | 6.6 | 3.6 |
| | 72 | 2.2 | 1.5 | 0.8 |
| A-5 | 1 | 2.2 | 1.7 | 2.1 |
| | 72 | 1.6 | 0.5 | — |
| A-6 | 1 | 2.6 | 2.8 | 2.1 |
| | 72 | 0.8 | 0.4 | — |
| A-7 | 1 | 1.8 | 1.7 | 0.5 |
| | 72 | 0.4 | 0.4 | — |
| A-8 | 1 | 2.6 | 1.3 | 0.5 |
| | 72 | 0.8 | 0.4 | — |
| A-9 | 1 | 13.8 | — | 8.2 |
| A-10 | 1 | 3.2 | — | 2.5 |
| A-11 | 1 | 4.2 | — | 3.1 |
| A-12 | 1 | 13.9 | — | 5.8 |
| A-13 | 1 | 2.9 | — | 3.4 |
| A-14 | 1 | 2.9 | — | 3.8 |
| A-15 | 1 | 2.8 | — | 3.6 |
| A-16 | 1 | 2.9 | — | 3.8 |
| A-17 | 1 | 3.6 | — | 3.2 |
| A-18 | 1 | 20.3 | — | 22.5 |
| A-19 | 1 | 4.4 | — | 4.5 |
| A-20 | 1 | 9.4 | — | 4.6 |
| | 72 | 2.6 | — | — |
| A-21 | 1 | 20.0 | — | 11.5 |
| | 72 | 3.1 | — | — |
| A-22 | 1 | 18.1 | | |
| A-23 | 1 | 21.5 | | |
| IV | 1 | 8.1 | — | 3.3 |

Table D presents additional data for the activity of compounds A-1 and A-4 against various cell lines. In some instances, comparative data against leptomycin B (LMB) and/or compound VI (Dong et al., US 2005/0272727 A1 (2005) is also provided.

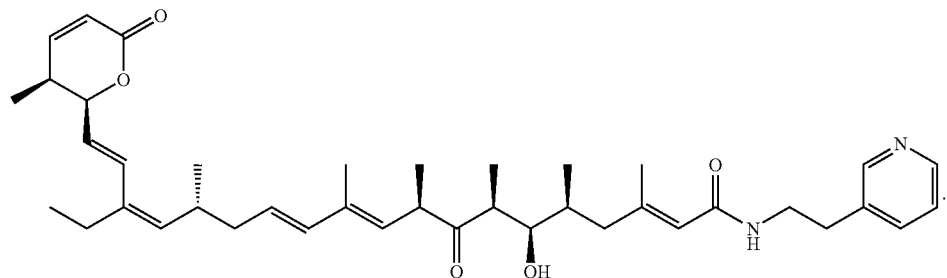

(VI)

TABLE D

| Cancer Cell Line | Exposure time (h) | LMB | VI | A-1 | A-4 |
|---|---|---|---|---|---|
| 22Rv1 | 1 | — | 1.8 | — | 4.6 |
|  | 72 | — | 0.3 | — | 0.7 |
| A-498 | 1 | — | 4.8 | 16 | 16 |
| A549 | 1 | — | 3.8 | 23.5 | — |
|  | 72 | 0.55 | 3 | — | — |
| BT474 | 1 | — | 2.1 | — | 3.8 |
|  | 72 | — | 0.8 | — | 2.3 |
| Caki-1 | 1 | — | 4.5 | 6.6 | — |
| CAL-27 | 1 | — | 0.7 | — | 2.8 |
|  | 72 | — | 0.3 | — | 0.5 |
| CCRF-CEM | 72 | — | 0.8 | 4.2 | — |
| Colo829 | 1 | — | 2.1 | — | 4.6 |
|  | 72 | — | 0.3 | — | 0.9 |
| FaDu | 1 | — | 7.3 | — | 27.9 |
|  | 72 | — | 1.0 | — | 1.6 |
| HCC1937 | 1 | — | 5.7 | — | 42.3 |
|  | 72 | — | 4.3 | — | 7.3 |
| HepG2 | 1 | — | 3.2 | — | 7.8 |
|  | 72 | — | 0.7 | — | 0.8 |
| LoVo | 1 | — | 2.5 | 10.3 | — |
| LS411N | 1 | — | 2.9 | — | 9.4 |
|  | 72 | — | 0.5 | — | 1.6 |
| LS513 | 1 | — | 5.5 | — | 6.3 |
|  | 72 | — | 0.9 | — | 1.0 |
| MDA-MB-468 | 1 | — | — | 30.6 | — |
| Mia-PaCa2 | 1 | — | 5.0 | — | 49.7 |
|  | 72 | — | 1.7 | — | 10.8 |
| MOLT-4 | 72 | — | 2.9 | 3.2 | — |
| NCI-ADR | 1 | 33.8 | 77.3 | 194 | 771 |
|  | 72 | — | 13 | 20.6 | 71.3 |
| NCI-H23 | 1 | — | 2.6 | — | 8.5 |
|  | 72 | — | 0.4 | — | 1.3 |
| NCI-H358 | 1 | — | 1.6 | — | 5.6 |
|  | 72 | — | 0.4 | — | 0.7 |
| OVCAR-4 | 1 | — | 6.7 | — | 80 |
|  | 72 | — | 1.5 | — | 8.8 |
| PC-3 | 1 | — | 3.3 | 7.4 | — |
|  | 72 | — | 0.7 | 2.7 | — |
| U87MG | 1 | — | 5.0 | — | 25.5 |
|  | 72 | — | 0.6 | — | 1.5 |
| UM-UC-3 | 1 | — | 2.6 | — | 7.0 |
|  | 72 | 0.3 | 0.3 | — | 1.4 |
| SKNSH | 1 | 4.1 | 2.2 | 5.1 | — |
|  | 72 | 0.4 | 0.5 | 1.5 | — |

The additional cell lines tested against represent a variety of different cancers: bladder cancer (UM-UC-3), breast cancer (BT474, HCC1937, MDA-MB468, NCI-ADR), CNS cancer (U87MG (glioma), SKNSH (neuroblastoma)), colon cancer (LoVo, LS411N, LS513), head and neck cancer (CAL-27, FaDu), leukemia (CCRF-CEM, MOLT-4), liver cancer (HepG2), lung cancer (A549, NCI-H23, NCI-H358), melanoma (Colo829), ovarian cancer (OVCAR-4), pancreatic cancer (BxPC-3, Mia-PaCa2), prostate cancer (22Rv1, PC-3), and renal cancer (A-498, Caki-1).

In summary, the data in Tables C and D show that compounds of this invention are effective for treating a variety of cancers, namely bladder cancer, breast cancer, cervical cancer, CNS cancer, colon cancer, head and neck cancer, leukemia, liver cancer, lung cancer, melanoma, ovarian cancer, pancreatic cancer, prostate cancer, and renal cancer.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having a structure represented by formula I

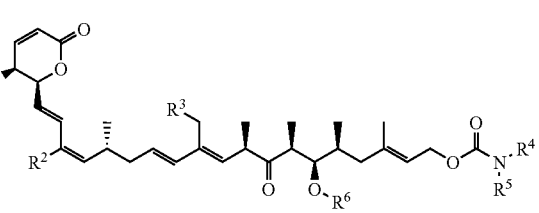

(I)

or a pharmaceutically acceptable salt thereof,
where
$R^1$ is H or methyl;
$R^2$ is methyl or ethyl;
$R^3$ is H;
$R^4$ and $R^5$ are independently, for each occurrence thereof, H, $C_1$-$C_8$ alkyl, $C_2$-$C_8$ alkenyl, $C_2$-$C_8$ alkynyl, $CHR^7R^9$, or (CHR$^9$)$_n$R$^8$, or R$^4$ and R$^5$ together with the nitrogen to which they are bonded combine to form

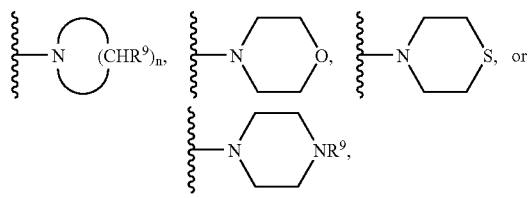

with the proviso that R$^5$ can also be C(=O)NH$_2$;
R$^6$ is H or C(=O)NR$^4$R$^5$;
R$^7$ is unsubstituted or substituted aryl, unsubstituted or substituted heteroaryl, unsubstituted or substituted cycloaliphatic, unsubstituted or substituted heterocycloaliphatic, CO$_2$R$^9$, cyano, or COR$^9$;
R$^8$ is unsubstituted or substituted aryl, unsubstituted or substituted heteroaryl, unsubstituted or substituted cycloaliphatic, unsubstituted or substituted heterocycloaliphatic, NR$^4$R$^5$, CO$_2$R$^9$, OH, halo, cyano, OR$^9$, or COR$^9$;
R$^9$ is, independently for each occurrence thereof, H, OH or C$_1$-C$_5$ alkyl; and
n is, independently for each occurrence thereof, 2, 3, 4, 5, or 6.

2. A compound according to claim 1, having a structure represented by formula I-a:

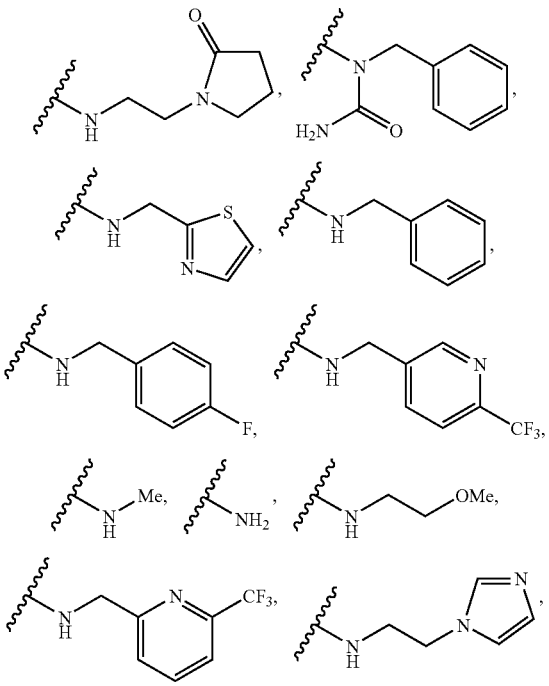

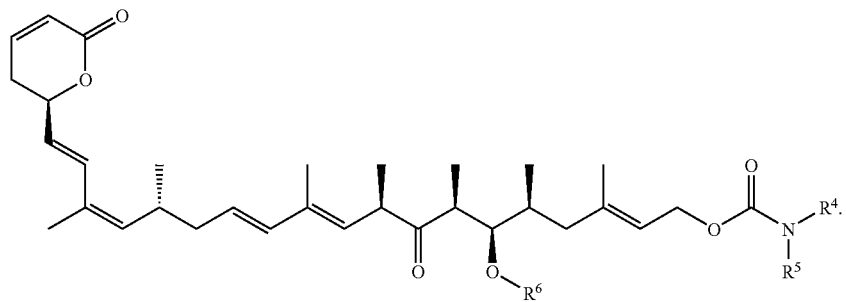

(I-a)

3. A compound according to claim 2, wherein NR$^4$R$^5$ is selected from the group consisting of:

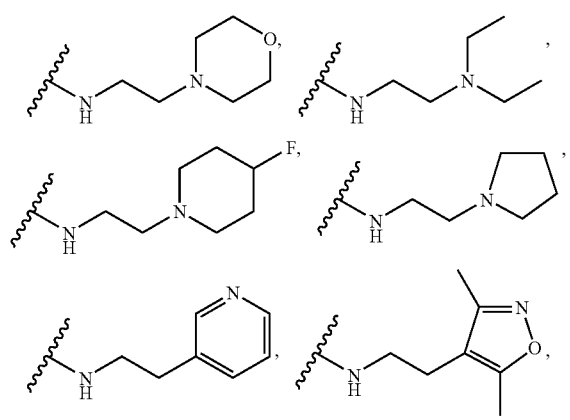

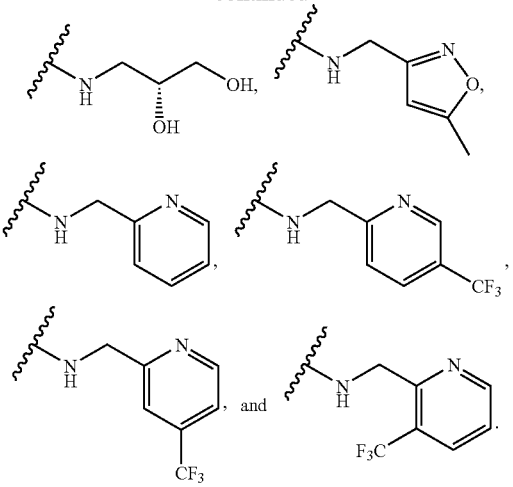

4. A compound according to claim 2, selected from the group consisting of
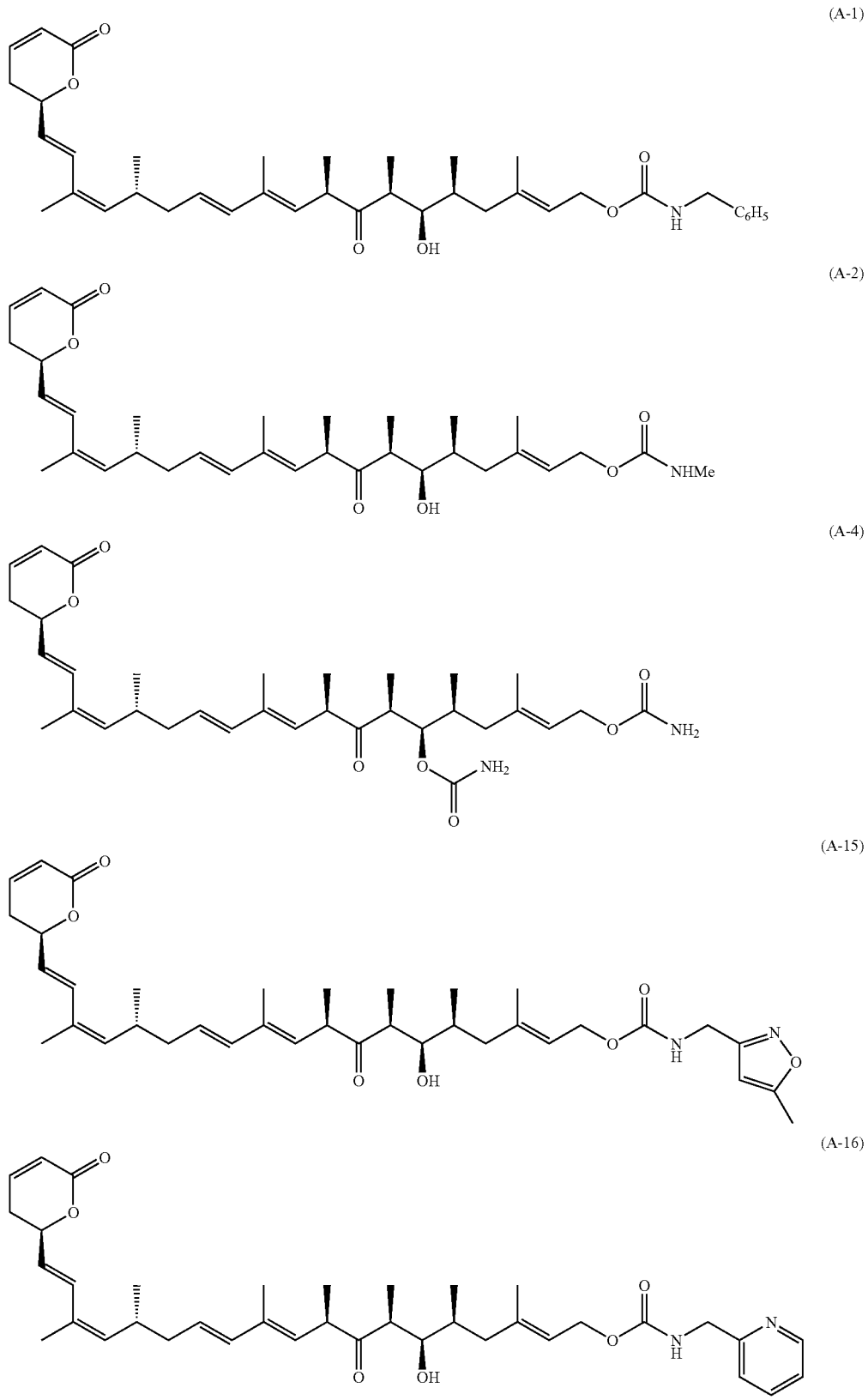

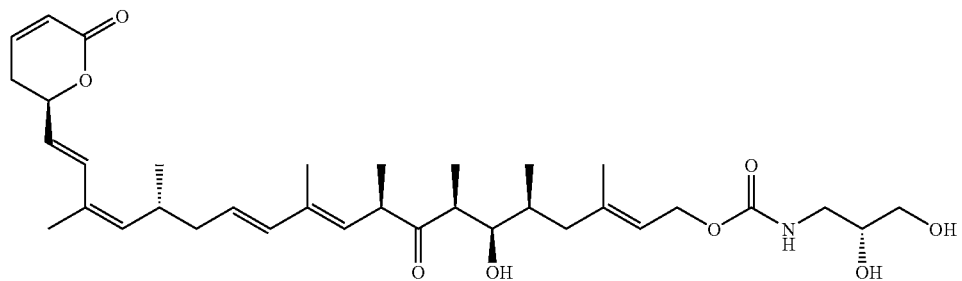
(A-17)
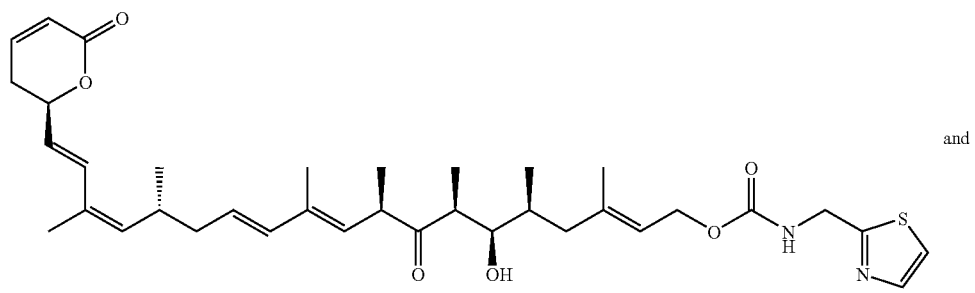
(A-19)
and
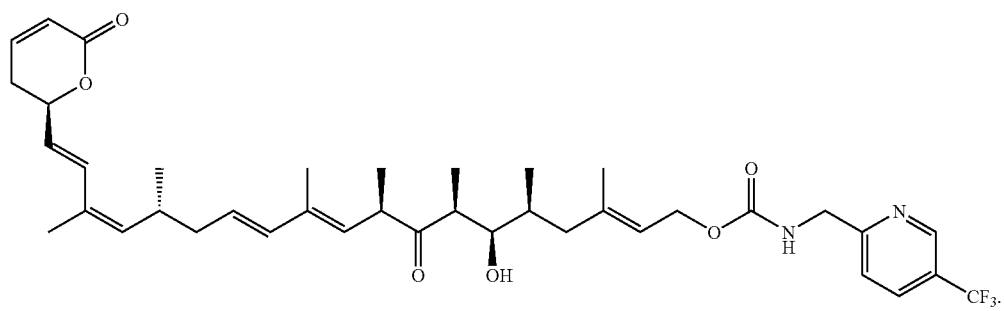
(A-21)
5. A compound according to claim 2, wherein $NR^5R^6$ contains a trifluoromethyl-substituted pyridyl moiety and $R^6$ is H.
6. A compound according to claim 5, selected from the group consisting of
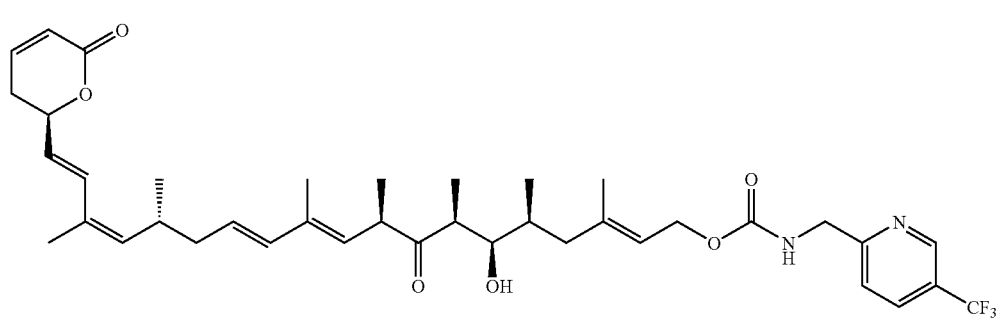
(A-21)

-continued
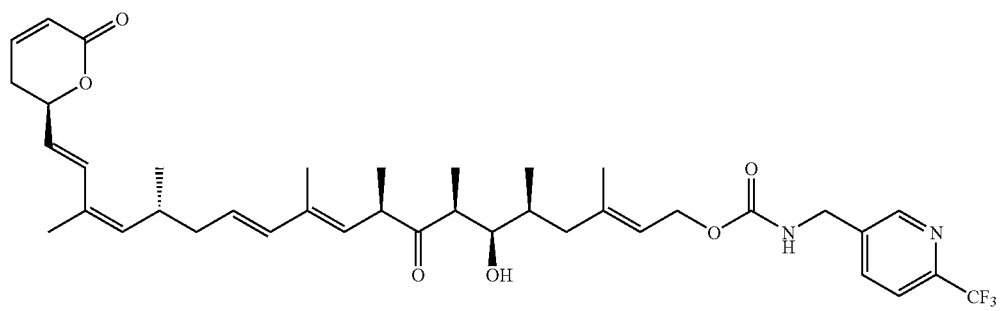
(A-22)
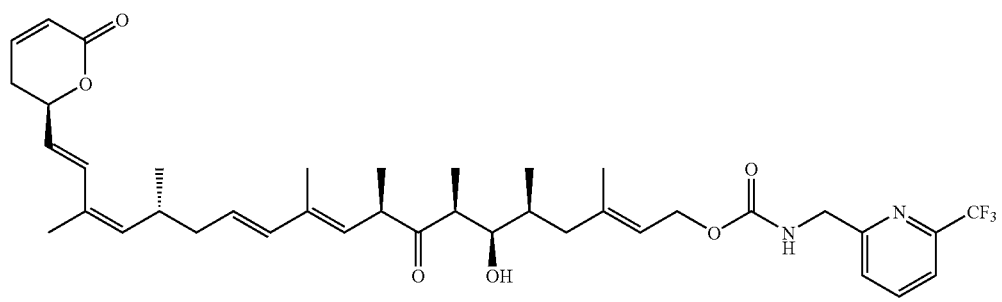
(A-23)
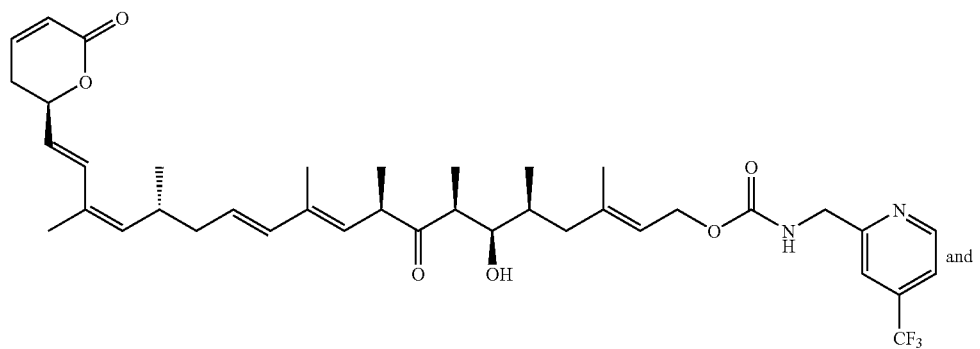
(A-24)
and
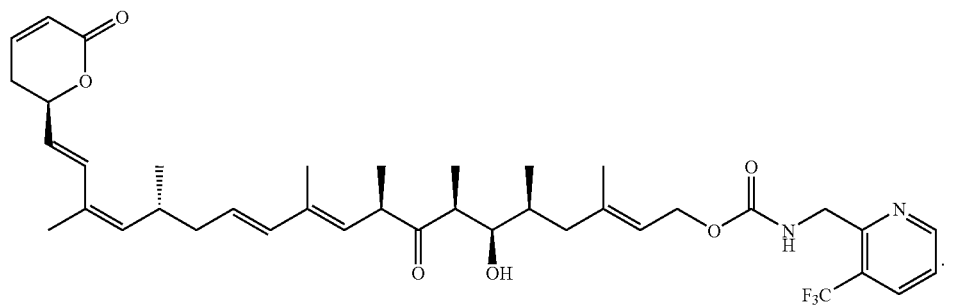
(A-25)

7. A compound according to claim 2, having a structure represented by formula A-4:
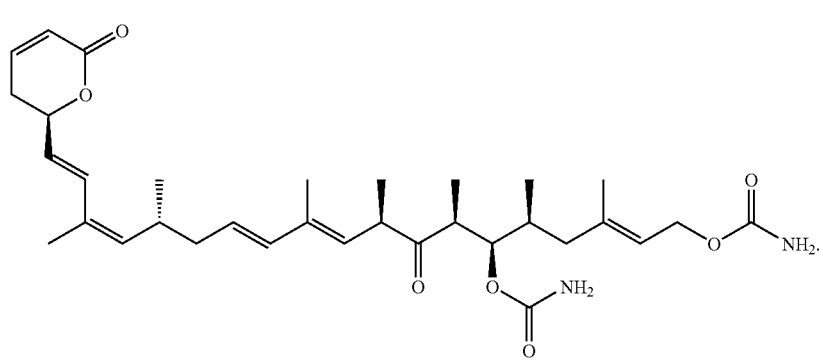
8. A pharmaceutical formulation comprising a compound according to claim 1 and an excipient.
9. A compound having a structure represented by formula (IV):
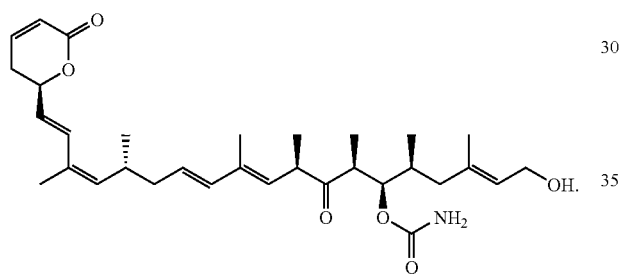
* * * * *

UNITED STATES PATENT AND TRADEMARK OFFICE
CERTIFICATE OF CORRECTION

PATENT NO. : 7,795,457 B2  Page 1 of 1
APPLICATION NO. : 12/070835
DATED : September 14, 2010
INVENTOR(S) : Hong Fu et al.

It is certified that error appears in the above-identified patent and that said Letters Patent is hereby corrected as shown below:

In the Claims:

Claim 3:

Column 39, lines 56 to 60, change

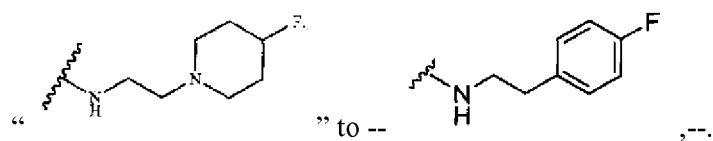 " to --  ,--.

Signed and Sealed this
Twenty-ninth Day of November, 2011

David J. Kappos
*Director of the United States Patent and Trademark Office*